(12) United States Patent
Gauthier et al.

(10) Patent No.: US 8,080,591 B1
(45) Date of Patent: *Dec. 20, 2011

(54) METHOD AND DEVICE FOR FABRICATING AEROGELS AND AEROGEL MONOLITHS OBTAINED THEREBY

(76) Inventors: Ben M. Gauthier, Washington, DC (US); Ann M. Anderson, Scotia, NY (US); Smitesh Bakrania, Ann Arbor, MI (US); Mary K. Mahony, Schenectady, NY (US); Ronald B. Bucinell, Niskayuna, NY (US)

( * ) Notice: Subject to any disclaimer, the term of this patent is extended or adjusted under 35 U.S.C. 154(b) by 996 days.

This patent is subject to a terminal disclaimer.

(21) Appl. No.: 12/021,505

(22) Filed: Jan. 29, 2008

Related U.S. Application Data

(63) Continuation of application No. 10/926,901, filed on Aug. 26, 2004, now Pat. No. 7,384,988.

(60) Provisional application No. 60/498,329, filed on Aug. 26, 2003.

(51) Int. Cl.
*C08J 9/00* (2006.01)
*B01J 13/00* (2006.01)

(52) U.S. Cl. ............... 521/64; 521/154; 264/621

(58) Field of Classification Search ............... 521/64, 521/154; 264/621
See application file for complete search history.

(56) References Cited

U.S. PATENT DOCUMENTS

| | | | |
|---|---|---|---|
| 2,249,767 A | 7/1937 | Kistler | |
| 4,432,956 A | 2/1984 | Zarzycki et al. | |
| 4,598,006 A | 7/1986 | Sand et al. | |
| 5,128,382 A | 7/1992 | Elliott et al. | |
| 5,252,620 A | 10/1993 | Elliott et al. | |
| 5,473,826 A | 12/1995 | Kirkbir et al. | |
| 5,686,031 A | 11/1997 | Coronado et al. | |
| 5,840,774 A | 11/1998 | Ehrlich et al. | |
| 5,869,545 A | 2/1999 | Biesmans et al. | |
| 5,958,363 A | 9/1999 | Coronado | |
| 5,973,015 A | 10/1999 | Coronado et al. | |
| 6,077,876 A | 6/2000 | Mendenhall et al. | |
| 6,090,861 A | 7/2000 | Mendenhall et al. | |
| 6,099,792 A | 8/2000 | Ganguli et al. | |

FOREIGN PATENT DOCUMENTS

SU 1680623 9/1991

OTHER PUBLICATIONS

Declaration of Ben M. Gauthier under 37 CFR 1.132.
Exhibit 1 to Declaration of Ben M. Gauthier under 37 CFR 1.132, weekly progress report (Jan. 6 to Mar. 10, 2002).

(Continued)

*Primary Examiner* — Irina S Zemel
(74) *Attorney, Agent, or Firm* — Nixon Peabody LLP

(57) ABSTRACT

Method and devices for rapidly fabricating monolithic aerogels, including aerogels containing chemical sensing agents, are disclosed. The method involves providing a gel precursor solution or a pre-formed gel in a sealed vessel with the gel or gel precursor at least partially filling the internal volume of the vessel and the sealed vessel being positioned between opposed plates of a hot press; heating and applying a restraining force to the sealed vessel via the hot press plates (where the restraining force is sufficient to minimize substantial venting of the vessel); and then controllably releasing the applied restraining force under conditions effective to form the aerogel. A preferred device for practicing the method is in the form of a hot press having upper and lower press plates, and a mold positioned between the upper and lower plates. Doped aerogel monoliths and their use as chemical sensors are also described.

11 Claims, 13 Drawing Sheets

OTHER PUBLICATIONS

Exhibit 2 to Declaration of Ben M. Gauthier under 37 CFR 1.132, Power Point presentation made at the ASME Speaking Competition (Apr. 13, 2002).

Watkins et al., "Portable, Low-Cost, Solid-State Luminescence-Based 02 Sensor", Applied Spectroscopy, 52 (5):750-754 (1998).

Scherer et al., "Optimization of the Rapid Supercritical Extraction Process for Aerogels", Journal of Non-Crystalline Solids, 311:259-272 (2002).

Tang et al., "Sol-Gel-Derived Sensor Materials That Yield Linear Calibration Plots, High Sensitivity, and Long-Term Stability", Analytical Chemistry, 75(10):2407-2413 (2003).

Cho et al., "Optical Sensor Array and Integrated Light Source", Analytical Chemistry, 73(14):3289-3293 (2001).

Xu et al., "A Real-Time Ratiometric Method for the Determination of Molecular Oxygen Inside Living Cells Using Sol-Gel-Based Spherical Optical Nanosensors With Applications to Rat C6 Glioma", Analytical Chemistry, 73 (17):4124-4133 (2001).

Amao et al., "Platinum Porphyrin Embedded in Poly(1-Trimethsylsilyl-1-Propyne) Film as an Optical Sensor for Trace Analysis of Oxygen", Analyst, 125:1911-1914 (2000).

Lee et al., "Optical Sensor for Oxygen Using a Porphyrin-doped Sol-Gel Glass", Analyst, 122:81-84 (1997).

Wolfbeis, "Fiber-Optic Chemical Sensors and Biosensors", Analytical Chemistry, 72:81R-89R (2000).

Baker et al., Effects of Processing Temperature on the Oxygen Quenching Behavior of Tris(4,7'-diphenyl-1,10'—phenanthroline) Ruthenium (II) Sequestered Within Sol-Gel-Derived Xerogel Films, J. Sol-Gel Science Technology, 17:71-82 (2000).

Poco et al., "A Rapid Supercritical Extraction Process for the Production of Silica Aerogels", Mat. Res. Soc. Symp. Proc., 431:297-302 (1996).

ASME Newsletter, May 2002.

ASME Newsletter, Jun. 2002.

Bakrania et al., "Characterization of Silica-Aerogels Fabricated Using a Novel Processing Technique", Mar. 2003, On-line Article http://www.vu.union.edu/~bakrania/aerogels/poster.jpg.

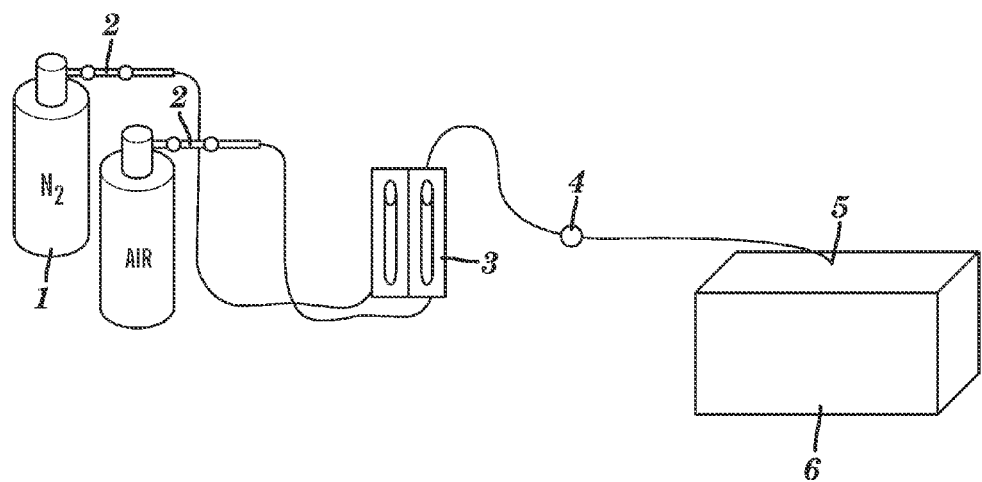
*FIG. 9A*
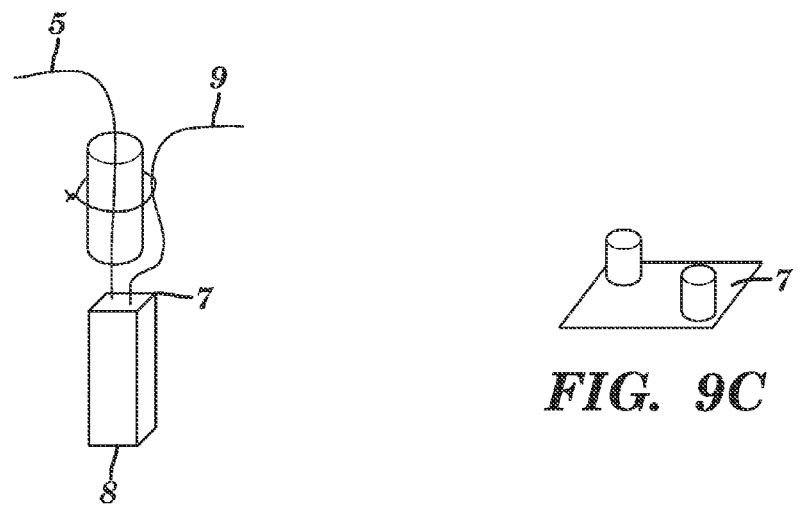
*FIG. 9B*
*FIG. 9C*

METHOD AND DEVICE FOR FABRICATING AEROGELS AND AEROGEL MONOLITHS OBTAINED THEREBY

This application is a continuation of U.S. patent application Ser. No. 10/926,901, filed Aug. 26, 2004, now U.S. Pat. No. 7,384,988 which claims the priority benefit of U.S. Provisional Patent Application Ser. No. 60/498,329, filed Aug. 26, 2003, each of which is hereby incorporated by reference in its entirety.

STATEMENT OF GOVERNMENT SPONSORSHIP

The present invention was made with funding received from the National Science Foundation under grant CTS-0216153. The U.S. government has certain rights in the invention.

FIELD OF THE INVENTION

The present invention relates generally to methods and devices for fabricating aerogels, monolithic aerogel products, and their use.

BACKGROUND OF THE INVENTION

Silicate precursors, such as tetramethoxysilane (Si(OCH$_3$)$_4$, "TMOS"), are commonly used to produce porous silica glasses (Brinker et al., *Sol-Gel Science*, Academic Press, New York (1990)). The resultant materials are highly crosslinked polymer matrices with solvent filled pore spaces. This solvent can be evacuated from the pore-matrix either by evaporation or by supercritical extraction; the two methods yield materials with different physical properties. During solvent evaporation, surface tension, which exists at any liquid-vapor interface, exerts a force large enough to collapse the pore structure until the gel network becomes strong enough to resist this compressive force (Brinker et al., *Sol-Gel Science*, Academic Press, New York (1990)). This process generates a condensed silicate matrix, referred to as a xerogel, which is made up of 60-90% air and has pore diameters of 1-20 nm (Brinker et al., *Sol-Gel Science*, Academic Press, New York (1990)). Evacuating the solvent above its critical point, where neither liquid nor gas is present, can eliminate the surface tension. Consequently, the pore structure does not collapse, but is instead maintained, yielding a low-density solid known as an aerogel (Pierre et al., *Chem. Rev.* 102:4243 (2002)). Aerogels typically consist of 90-99% air (Lev et al., *J. Gun, Anal. Chem.* 67:22A (1995)), with pore diameters from 1-50 nm (Brinker et al., *Sol-Gel Science*, Academic Press, New York (1990)).

The resulting aerogel structure is responsible for giving aerogel materials claim to the lowest known density, index of refraction, thermal, electrical, and acoustical conductivities of any solid material. First discovered by Kistler (*J. Phys. Chem.* 63: 52 (1932)) in the 1930s, many attempts have been made to take advantage of their unique properties. Current application areas include Cerenkov radiation detectors (Ganezer et al., *IEEE Trans. Nucl. Sci.* 41:336 (1994); Hasegawa et al., *Nucl. Inst. Phys. Res.* 342:383 (1994)), electronics (Hrubesh et al., *J. Non-Cryst. Solids* 188:46 (1995)), thermal insulators (Reiss, *Phys. Blaetter* 48:617 (1992)), insulated windows (Hrubesh et al., *J. Non-Cryst. Solids* 188:46 (1995); Lampert, *Int. J. Energy Res.* 7:359 (1983)), comet dust collectors (Tsou, *J. Non-Cryst. Solids* 186:415 (1995)), and heat storage devices for automobiles (Fricke et al., *J. Sol-Gel Sci. Technol.* 13:299 (1998)).

At present, aerogel materials are difficult and expensive to manufacture. It can take days to weeks to make an unbroken monolith. This manufacturing complexity has limited their development in commercial applications. Aerogels are typically formed in a two-step process. The first step is to form a wet gel by a sol-gel polymerization reaction. The second step is to extract the solvent and dry the wet gel to form the aerogel.

The primary challenge in the fabrication of an aerogel is to prevent the collapse of the porous structure during the drying phase. Stress contributors such as thermal gradients and pressure concentrations are significant in aerogel fabrication, but relatively easy to minimize. More difficult to control, however, are the capillary stresses from surface tension that, for the nanoscale pore structure, are strong enough to cause structural collapse. As the sol-gel dries, these capillary forces can result in significant fracture to the structure. The current methods used to avoid fracture in aerogel fabrication can be categorized into three general techniques, although each drying protocol is designed to minimize or eliminate surface-tension effects. They are (1) ambient pressure techniques; (2) conventional supercritical extraction (CSCE) techniques; and (3) rapid supercritical extraction (RSCE) techniques.

The ambient-pressure techniques attempt to dry the wet gel at ambient pressure. To do so they require chemical processes to reduce the capillary forces. One method is to treat the surface of the gel with a surfactant, or surface-tension-reducing chemical (see, e.g., Yusuf et al., *J. Non-Cryst. Solids* 285:90 (2001); or Lev et al., *Anal. Chem.* 67:22A (1995)). Another technique used by Hereid et al. (*J. Sol-Gel Sci. Technol.* 3:199 (1994)) ages the gels in alkoxide/alcohol solutions to stiffen the microstructure and avoid collapse due to capillary forces. A technique developed by Prakash et al. (*J. Non-Cryst. Solids* 190:264 (1995)) manipulates the surface chemistry of the gel to aid in the solvent evacuation. This method uses a solvent exchange with hexane, followed by a surface modification with a silylation process to promote a reversible shrinkage. These techniques have been used successfully in the fabrication of aerogel films, but have had limited success for aerogel monoliths.

The conventional supercritical extraction techniques (CSCE) are multi-step techniques designed to eliminate surface tension altogether by bringing the sol-gel to the critical point of the solvent. Above the critical point there is no surface tension, and the solvent can be evacuated without damage to the gel structure. The technique first developed by Kistler (*J. Phys. Chem.* 63: 52 (1932)) entailed two steps: the formation of the wet gel, and the subsequent solvent evacuation in a heated pressure vessel at the supercritical conditions. The main limitations of this technique are the difficulties associated with obtaining the high temperatures necessary to reach the critical point of the alcohol solvent, as well as the safety concerns with operating the pressure vessel at those conditions. In response to these concerns, a lengthy solvent exchange with liquid CO$_2$ can be performed prior to supercritical extraction, which can then take place at the critical point of CO$_2$ (see, e.g., Tewari et al., in *Aerogels*, J. Fricke (Ed.), Springler-Verlag, New York (1986), p. 31; Van Bommel et al., *J. Non-Cryst. Solids* 186:78 (1995)). The advantages of the CSCE method are a lower critical temperature and a more stable solvent; however an additional step is added to the process. Because the critical pressure requirement is not changed significantly, this process still requires the use of thick pressure vessels and places practical limitations on the maximum size of the aerogel. In addition, the solvent-exchange process becomes a size deterrent, as the diffusion kinetics of the solvent exchange depend upon the size of the gel. Even if a pressure vessel were available to contain a large monolith, the solvent exchange could take weeks to complete, depending on the size of the monolith.

The third technique, rapid supercritical extraction (RSCE), was developed by Poco et al. (*Mat. Res. Soc. Symp.* 431:297 (1996)) and described further in Scherer et al. (*J. Non-Cryst. Solids* 311:259 (2002)). Similar to the CSCE techniques, RSCE is a supercritical technique designed to perform the solvent extraction under supercritical conditions. In contrast to the CSCE techniques, however, the RSCE is a one-step, reactant-to-aerogel process. The liquid precursor chemicals and catalyst are inserted into a two-piece mold that is then heated rapidly to speed up the polymerization. The pressure is initially set by fastening the two mold parts together with properly tensioned bolts, or by applying an external hydrostatic pressure inside of a larger pressure vessel, or by a combination of these two. Once the supercritical point of the alcohol is reached, the supercritical fluid is allowed to escape through gaps formed by the roughness in the surface contact between the two portions of the mold, or through a relief valve set just above the supercritical pressure. A benefit of this method is that the entire process is done in one step, and can be accomplished in under an hour, as opposed to multiple steps (and time scales on the order of weeks) for all other available methods.

The advantage of the ambient-pressure methods is that they do not require expensive and potentially dangerous pressure equipment. They are currently being used successfully in the fabrication of aerogel powders and thin films. For the fabrication of monolithic pieces, however, this technique has yet to prove reliable. Conventional supercritical extraction has been used extensively in the fabrication of very large aerogel monoliths, however it can take days to weeks to make them, and the required multiple steps make the process complicated. In addition to the reduction in fabrication time, the rapid supercritical extraction as a one-step process has the most potential for reliable and repeatable fabrication, as well as increased production volume.

The present invention relates to a fast supercritical extraction technique for fabricating aerogels that overcomes the above-identified deficiencies of the prior art.

SUMMARY OF THE INVENTION

A first aspect of the present invention relates to a method for rapidly producing aerogels that includes the steps of: providing a gel precursor solution or a pre-formed gel in a sealed vessel with the gel or gel precursor at least partially filling the internal volume of the vessel and the sealed vessel being positioned between opposed plates of a hot press; heating and applying a restraining force to the sealed vessel via the hot press plates; and controllably releasing the applied restraining force under conditions effective to form the aerogel.

A second aspect of the present invention relates to a method for rapidly producing aerogels that includes the steps of: heating and applying external restraining force to a sealed vessel that contains therein a gel precursor solution or a pre-formed gel that at least partially fills the internal volume of the sealed vessel, said heating and applying external restraining force being carried out without substantial venting of the vessel and thereby confining physical expansion of the gel or gel precursor; and controllably releasing the external restraining force applied to the vessel, thereby allowing for venting and release of internal pressure to form the aerogel.

A third aspect of the present invention relates to a device for forming aerogels that includes: a hot press having upper and lower press plates which can be manipulated toward and away from one another to apply or release force on a mold therebetween; and a mold positioned between the upper and lower plates of the hot press, the mold being adapted to confine an aerogel or precursors of the aerogel.

A fourth aspect of the present invention relates to an aerogel that is formed according to the first or second aspects of the present invention. A preferred form of aerogel contains embedded within the monolith one or more chemical sensing agents, such as a fluorescent dye or a fluorescent coordination complex.

A fifth aspect of the present invention relates to a chemical sensor that includes: a monolithic aerogel that contains one or more chemical sensing agents; a light source that illuminates the monolithic aerogel at an excitation wavelength of the chemical sensing agent; and a detector that detects an emission signal from the chemical sensing agent or transmitted light.

A sixth aspect of the present invention relates to a method of detecting a chemical in gas phase that includes the steps of: exposing a gas sample to the chemical sensor according to the fifth aspect of the present invention; and detecting a change in agent-emitted light or transmitted light, the change indicating presence of the chemical in the gas sample.

The process of the present invention offers a number of distinct advantages over existing techniques. The process is fast, simple, and easily automated, which may make it more amenable to large-scale assembly-line fabrication applications. The process is also safe. The hydraulic press provides a restraining force capable of (1) containing the internal pressure and (2) controllably releasing excess pressure. The only pressurized volume is the gel itself, not an entire hydrostatic volume as is the case when using an autoclave or an external hydrostatic pressure, as in the RSCE process. Additional safety concerns associated with the release of supercritical alcohol can be alleviated by encasing the inter-platen working area and flushing the working area with a nitrogen purge to eliminate the possibility of auto-ignition of hot solvent (e.g., methanol) should it escape from the mold and mix with air. By doping the aerogel precursors with fluorescent dyes or coordination complexes, it is possible to prepare chemical sensors that are cost- and time-effective, require little synthetic work, and can be easily adapted for simultaneous use with many of the current aerogel systems.

BRIEF DESCRIPTION OF THE DRAWINGS

FIG. 7A illustrates a four hole design, each hole preparing a single 1.5 inch diameter×¾ inch high aerogel. FIG. 7B illustrates a single hole design, the hole preparing a single ¾ inch diameter×1 inch high aerogel. FIG. 7C illustrates a twenty-five hole design, each hole preparing a ⅜ inch diameter×¾ inch high aerogel.

FIG. 8A shows the structure of tris(2,2'-bipyridyl)ruthenium(II); FIG. 8B shows the structure of ruthenium(II) 4,7-diphenyl-1,10-phenanthroline; and FIG. 8C shows the structure of platinum octaethylporphine.

FIGS. 9A-C illustrate a gas-mixing system. In FIG. 9A, gaseous nitrogen and ultrapure air (1) are delivered to TYGON® tubing via two-stage regulators (2), the gases are mixed in a gas proportioner (3), and then pass through a line regulator (4) and an injection port (5) to a fluorimeter (6). In FIG. 9B, the gas mixture then flows through inlet port (5) and the tubing is fed into a cuvette through a modified cuvette cap (7). The sample is held in the cuvette (8). The gas mixture is vented into the fluorimeter chamber through a piece of TYGON® tubing (9). FIG. 9C shows two holes bored into the top of a cuvette cap (7). TYGON® tubing was threaded snugly through those holes.

DETAILED DESCRIPTION OF THE INVENTION

Figure 1:
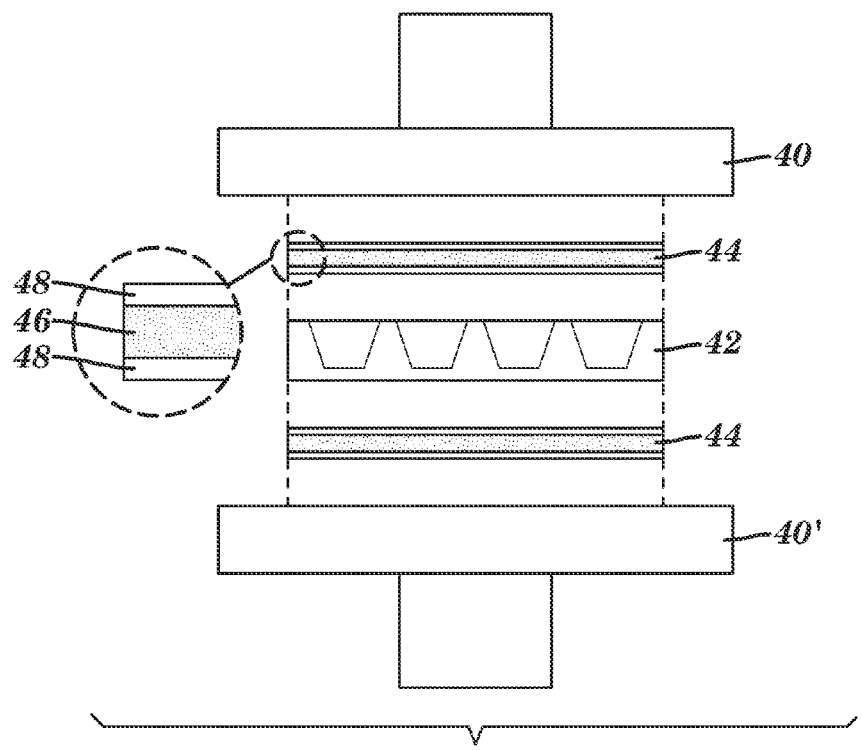
FIG. 1 is a schematic illustration of a mold and press configuration for aerogel processing. A preferred configuration includes a stainless-steel aerogel mold sandwiched between Kapton and a high-temperature gasket material. The hydraulic hot press provides a restraining force during processing.

The present invention relates generally to methods and devices for the one-step fabrication of monolithic aerogel products.

The device used in accordance with the processes of the present invention generally includes a hot press that has upper and lower press plates, and a mold positioned between the upper and lower plates of the hot press.

The hot presses that can be employed in the present invention can include either hydraulic or electronic regulation of the upper and lower press plates. One requirement for the hot press is that the hydraulically or electronically regulated press plates can be manipulated toward and away from one another to apply or release on a mold therebetween a restraining force that is sufficient to prevent and/or minimize any venting during the ramp-up and dwell phases of aerogel production. The heating mechanism employed on the hot press is preferably an electrical heating system that can achieve heating up to at least about 300° C., at rates of up to about 2° C./min. The hot press also needs to provide a restraining force sufficient to counter the internal pressure force created by the precursors in the mold, typically up to about 220 kN (50,000 lb). The hot press platen surfaces should be substantially parallel and flat to within at least about 0.13 mm (0.005 inches).

By way of example and without limitation thereto, a preferred type of hot press is 50-ton hydraulic hot press manufactured by Accudyne Engineering and Equipment Company (Bell Gardens, Calif.). Other suitable hot presses include those manufactured by Tetrahedron, Inc.

The mold includes a mold body and upper and lower seals positioned against upper and lower surfaces of the mold body. During use, the upper and lower seals contact, respectively, the upper and lower press plates of the hot press.

The mold body is preferably formed of a substantially smooth surfaced material that can sustain the thermal cycling without deformation, and has thermal properties that allow for uniform heating of the aerogel precursor or aerogel contained therein. Exemplary materials used for forming the mold include, without limitation, stainless steel, steel and aluminum.

The mold can be shaped and configured to any desired size or shape of the resulting aerogel monolith that is to be fabricated. The mold can contain any number of receptacles that are designed to retain individual aerogel or aerogel precursors (i.e., two or more) provided the wall thickness around each receptacle is sufficient to prevent deformation during processing. The mold surface, which contacts the seal (discussed below), is preferably a substantially planar surface, flat within about 0.013 mm (0.005 inches). The substantially planar surface of the mold ensures that a tight seal can be formed between the mold surface and the press plates, thereby minimizing or substantially precluding venting of the mold during ramp-up and dwell phases of the process. The mold surface can be sprayed with mold release, such as high temperature Teflon spray, to facilitate removal of the aerogels from the mold; however, this is not required for the process.

The seal against the upper and lower press plates is formed of a composite gasket that includes a high temperature gasket material sandwiched between high temperature sealant material. The sealant material is used to prevent the high temperature gasket material from adhering to the mold or platen surface. It is preferably about 0.025 to about 0.50 mm (1 to 2 mil) thick Kapton™ or Teflon™. Of these, Kapton™ is preferred. The high temperature gasket material is preferably about 0.8 to about 1.6 mm (1/32 to 1/16 inch) thick graphite, silicone rubber or Teflon™. Of these, graphite is preferred.

Aerogel precursor materials are widely known in the art, and any suitable aerogel precursor materials can be used to form aerogels according to the present invention. Known aerogel materials include silica, alumina, titania, hafnium carbide, various polymers, and chalcogenide semiconductors (e.g., CdSe, ZnS, PbS). By way of example, silica aerogels can be formed with tetralkoxysilanes such as TMOS in combination with alcohols such as methanol or ethanol, water, and a base such as ammonium hydroxide. The ratio of these materials can be adjusted as is known in the art to achieve aerogel properties that are optimized for particular end uses thereof.

In addition to the aerogel precursor materials, the aerogel precursor can be doped to include one or more chemical sensing agents. Any known dopants of the type used for thin sol-gel film sensors can be utilized as long as the dopants are stable at temperatures used in the process described hereinafter. Suitable chemical sensing agents include fluorescent dyes and fluorescent coordination complexes, and can be employed to interact with another chemical species of interest, for sensing applications, or used for fundamental studies of aerogel microstructure. Exemplary organic dyes include, without limitation, fluorescein, rhodamine B, rhodamine 6G, and 8-hydroxypyrene-1,3,6-trisulfonic acid. Exemplary fluorescent coordination complexes include, without limitation, tris(2,2'-bipyridyl)ruthenium(II) or $Ru(bpy)_3^{2+}$, ruthenium (II) 4,7-diphenyl-1,10-phenanthroline or $Ru(dpp)_3^{2+}$, and platinum octaethylporphine (PtOEP).

In practicing the method of fabricating aerogel monoliths in accordance with the present invention, a gel precursor solution or a pre-formed gel is first provided in a sealed vessel (i.e., the mold) with the gel or gel precursor at least partially filling the internal volume of the vessel and the sealed vessel being positioned between opposed plates of a hot press. The at least partially filled vessel can either be (1) filled, sealed, and then transferred to a position between the press plates or (2) positioned between the plates (i.e., supported by the lower plate), filled, and then sealed. Regardless of the approach used for filling and sealing the vessel, once the vessel has been positioned, aerogel formation can begin.

Aerogel formation is performed by heating and applying a restraining force to the sealed vessel via the hot press plates. The heating and applying of restraining force can be carried out simultaneously via the hot press plates; or the application of restraining force can be carried out prior to heating.

The restraining force is an external force (applied by the hot press via the plates) sufficient to counter the forces caused by the pressure increase in the sealed vessel that results from heating of the aerogel precursor materials. The restraining force to be applied will depend upon both the size of the mold and the amount of pressure which is expected to develop inside the vessel during the heating process. The estimated restraining force ($F_{rest}$) can be defined as:

$$F_{rest} = P_{mold} * A_{mold} \quad \text{Eq. (1)}$$

where $P_{mold}$ is the pressure in the mold, typically between 9 MPa and 17 MPa (1300 to 2500 psi) and $A_{mold}$ is the surface area of the mold. In general, the restraining force is at least about 70 kN.

By way of example, a restraining force of at least about 145 kN (32,500 lb), most preferably between 145 kN to about 280 kN is appropriate for a 5 inch by 5 inch mold containing four 1.5 inch-diameter receptacles.

The heating of the mold and aerogel precursor materials is carried out until a temperature above the supercritical temperature of the aerogel solvent is achieved. This is the ramp-up phase of heating. The ramp-up phase is carried out at a rate that is suitable to allow for aerogel development. Preferably the heating rate is up to about 2° C. per minute, more preferably between about 1° C. to about 2° C. per minute. The maximum temperature to be achieved is typically, though not exclusively, between about 240° C. to about 300° C.

Once the maximum temperature has been achieved, the temperature can optionally be maintained for a dwell or soak phase. During the optional dwell or soak phase, the restraining force applied to the sealed vessel is also preferably maintained (i.e., it is preferred that no venting occurs during this phase). The dwell or soak phase can be of any duration, more preferably between about 1 minute and about 60 minutes, most preferably between about 10 and about 30 minutes.

It is preferable that no substantial venting occurs during either the ramp-up phase or the optional dwell phase; however, some venting may occur to the extent that the internal pressure within the mold overcomes the restraining force applied externally of the mold via the hot press plates. To the extent that venting does occur (i.e., the restraining force is low enough to allow venting to occur), such venting should not allow internal pressure within the mold to drop below the critical point. Hence, the restraining force to be applied should be selected to always maintain the solvent in the supercritical state during ramp-up and any optional dwell phase.

After any optional dwell phase, the applied restraining force is controllably released under conditions effective to remove any remaining solvent from the sol-gel, thereby forming the aerogel. By controllably releasing, it is intended that a portion of the restraining force originally applied to the sealed vessel via the hot press plates is removed. The remaining restraining force is insufficient to prevent venting of the sealed vessel; hence, at this time supercritical fluid escapes from the vessel. By way of example, the remaining restraining force is preferably at least about 4 kN, more preferably between about 4 and about 30 kN Upon completion of any dwell phase, the temperature is also decreased to ambient temperature. The rate of temperature decrease can be up to about 5° C. per minute, more preferably between about 1° C. to about 4° C. per minute, most preferably between about 2° C. to about 3° C. per minute. Upon reaching ambient temperature, any remaining restraining force is removed. Thus, the plates of the hot press are retracted, allowing for collection of the resulting aerogels.

It is important to note that the time required to prepare the aerogels in accordance with the present invention is preferably not more than about 12 hours, more preferably not more than about 9 hours, and most preferably not more than about 6 hours. Process times of as little as approximately 5 hours have been achieved.

As noted above, the aerogel can be doped with one or more chemical sensor agents. Aerogels doped with such probes are particularly useful in preparing chemical sensors that are capable of detecting a chemical species in, e.g., a gas sample. Exemplary chemical species that can be detected include, without limitation, oxygen, carbon dioxide, carbon monoxide, and hydrocarbons.

The chemical sensor will include a doped aerogel of the present invention, a light source that illuminates the monolithic aerogel at an excitation wavelength of the chemical sensing agent, and a detector that detects an emission signal from the chemical sensing agent or transmitted light. Depending upon the position of the detector relative to the light source, the detector can measure either emissions from the chemical sensing agent (i.e., scattered light) or transmitted light that passes through the doped aerogel. In the latter embodiment, the detector is directly opposite the light source. In the former embodiment, the detector is laterally displaced from the light source such that it is not illuminated directly. Optionally, both types of detectors can be used simultaneously; that is, at least two detectors are present.

Suitable light sources include, without limitation, light emitting diodes, laser diodes, and any white light source such as flashlight bulbs (an incandescent bulb).

Suitable detectors include, without limitation, photodiodes, photomultiplier tubes, and charge-coupled detectors.

In addition to the light source and detectors, the sensor device can also include a housing that contains the monolithic aerogel and is provided with a passage for delivering a gas sample across the aerogel. The gas sample can be delivered passively or actively. The sensor housing should be optically transparent, at least in the range of light that used for illumination and for the range of light that is emitted by the chemical sensing agent.

One or more filters can also be utilized, either between the monolithic aerogel (i.e., the housing containing the same) and the light source, between the monolithic aerogel (i.e., the housing containing the same) and the detector, or both. Suitable filters include bandpass filters and longpass filters. It is preferable that the filter between the aerogel and the light source is a bandpass filter, whereas the filter between the aerogel and the detector(s) can be either a longpass filter or a bandpass filter.

The chemical sensor device can be coupled to an electrical control system that is designed to monitor the output of the detectors and, if necessary, sound an alarm when the quantity of the sensed chemical agent becomes too high or merely when its presence is detected. In the former sense, the sensor is a quantitative sensor. In the latter sense, the sensor is used merely as a non-quantitative switch.

Figure 15:
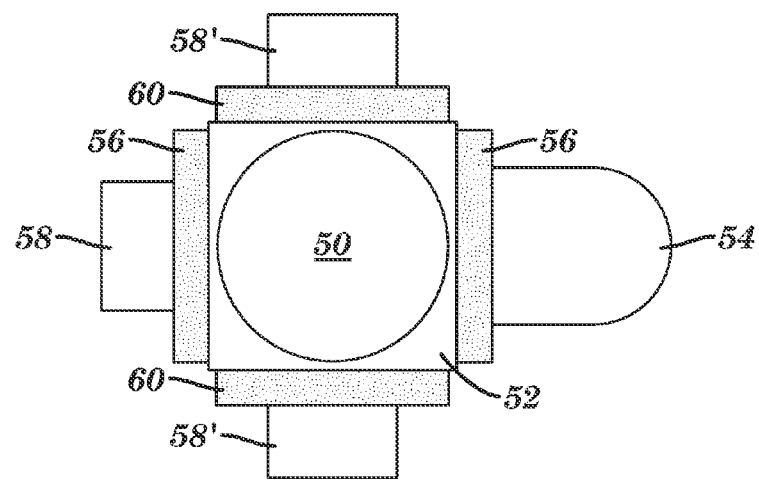
FIG. 15 is a top plan view of a gas sensor device that utilizes a doped aerogel containing a chemical sensor agent.
Figure 16:
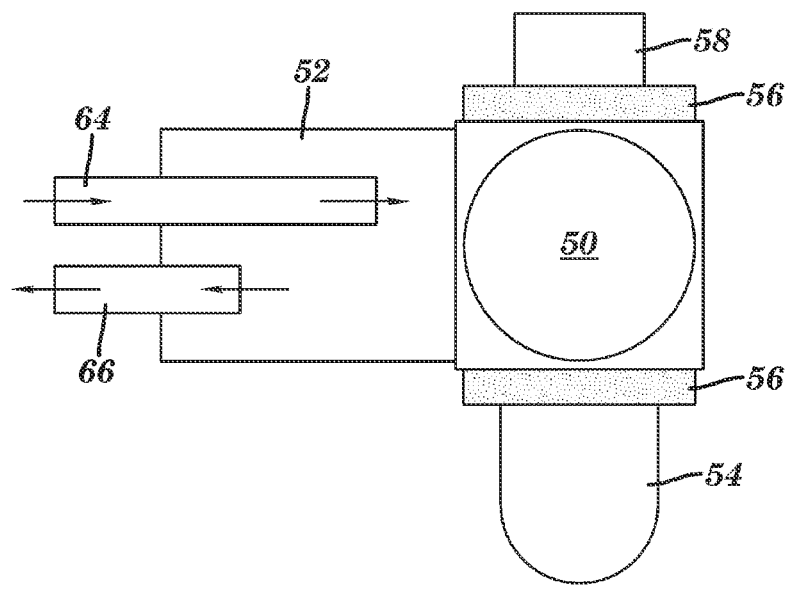
FIG. 16 is a side elevational view of the gas sensor device shown in FIG. 15, with one of the detectors omitted to expose the housing beneath.

An exemplary embodiment of the chemical sensor device is illustrated in FIGS. 15 and 16. In this embodiment, a doped aerogel forms the sensor element 50, which is present in an optically transparent housing 52. As shown in FIG. 16, the housing includes inlet 64 and outlet 66 passages for exposure of the aerogel to a vapor sample. The light source 54 (e.g., light emitting diode or laser diode) is positioned on one side of the housing, and three detectors 58, 58' (e.g., photodiodes) are positioned on three sides of the housing. The detector directly across from the light source is positioned to detect transmitted light. The detectors displaced 90 degrees from the light source are positioned to detect scattered light, such as that emitted by the chemical sensing agent present within the aerogel monolith. A bandpass filter 56 is provided between the housing and light source, as well as between the housing and detector 58. A longpass filter or bandpass filter 60 is provided between the housing and the detectors 58' to block light from excitation source, but transmit fluorescence intensity from the chemical sensing agent.

In use, the chemical sensor will be exposed to a gas sample that may contain the chemical species to be detected, and a change in agent-emitted light or transmitted light is detected after such exposure. Any change can indicate presence of the chemical species in the gas sample. As noted above, the sensor can in some circumstances be used to detect quantitatively the amount of the chemical species that is present in the gas sample.

EXAMPLES

The following examples are intended to illustrate, but by no means are intended to limit, the scope of the present invention as set forth in the appended claims.

Example 1

System for Aerogel Fabrication

Referring to FIG. 1, equipment used to fabricate the aerogel monoliths by the new fast supercritical extraction technique of the present invention includes a 50-ton hydraulic hot press (having upper and lower press plates 40, 40'), a stainless-steel mold 42, and a high-temperature seal 44 formed of a graphite gasket 46 sandwiched between sheets of Kapton™ film 46. By way of example, the mold 42 is fabricated from a 10×10×2 $cm^3$ thick piece of stainless steel (see FIG. 1). Sixteen 2.2 cm diameter, 1.7 cm-deep holes (with a 7° taper) are spaced uniformly across the plate. The surface was ground flat to ensure a good seal between the gasket and the mold.

Example 2

Fabrication of Aerogels

The system described in Example 1 above was used to prepare aerogels.

The one-step fabrication process entails two main phases, both of which take place inside of the mold during a continuous process. The first phase is to polymerize silica to form a sol-gel, and the second phase is to safely evacuate the water and alcohol solution. Initially, the chemical precursors for the aerogel were mixed and poured into the mold. For a tetramethoxysilane-derived (TMOS) aerogel, these precursors are TMOS, deionized water, methanol, and ammonium hydroxide with molar ratios TMOS:MeOH:$H_2O$:$NH_4OH$ of $1.0:12.0:4.0:3.7 \times 10^{-3}$.

The mold is placed in the hydraulic hot press and the processing begins by applying and holding a 75 kN restraining force. Typically, a temperature ramp of 1.25° $C.min^{-1}$ is applied to heat the mold from ambient temperature to a supercritical temperature (~265-300° C.). The internal pressure of the mold increases as a result of the temperature rise as dictated by the thermodynamics of the system. Following a 15-30 minute soak at supercritical conditions (for methanol, $T_{crit}$=240° C. and $P_{crit}$=8.1 MPa), the load is dropped to 4 kN, allowing supercritical fluid to escape, and the temperature is decreased at a rate of up to about 2.5° $C.min^{-1}$. Upon reaching ambient temperature, the platens of the hydraulic press retract, and the resulting aerogels are collected. The overall time to complete the process as described is 5 hours.

Figure 2:
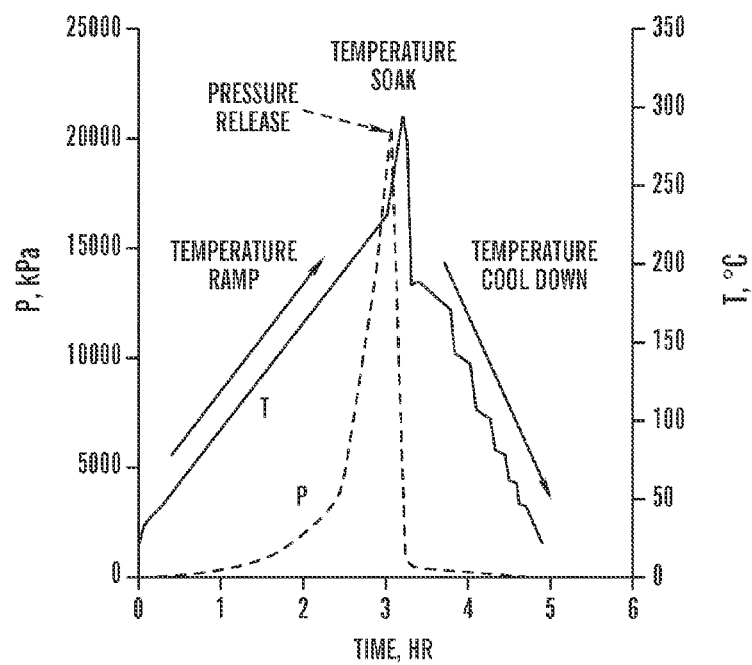
FIG. 2 is a graph illustrating the in-mold temperature (thick line) and pressure (thin line) data for aerogel processing shows the temperature ramp, soak and cool down processes that occur during a 5 hour cycle. For this test, the temperature ramp rate was set at 1.1° $C.min^{-1}$ and cool down rate at ~5° $C.min^{-1}$.
Figure 3:
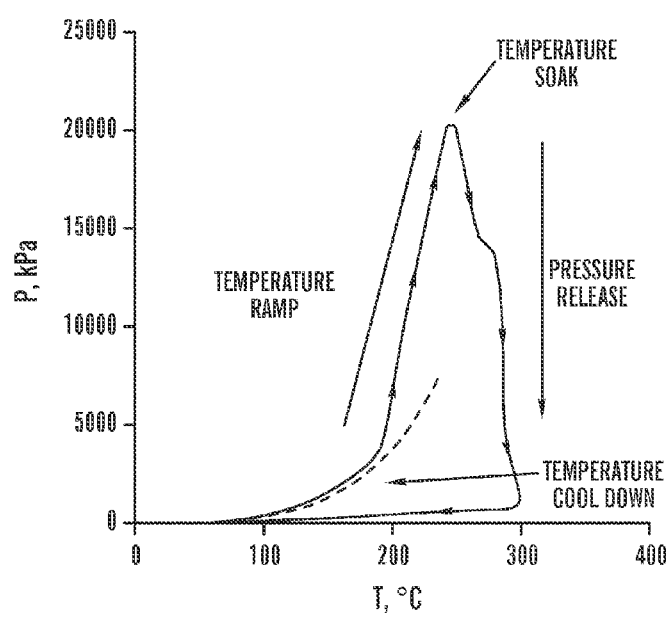
FIG. 3 is a graph illustrating the pressure versus temperature data for the 5 hour process depicted in FIG. 2, and shows that the solution stays above the methanol liquidus line (indicated by dashed line) until critical temperature and pressure are reached.

Process temperature and pressure data were acquired by instrumenting the mold with a melt pressure transducer. FIG. 2 plots the temperature and pressure data as a function of time and FIG. 3 plots pressure versus temperature superimposed on a methanol liquidus line (indicated by the dashed line). The temperature ramp phase lasted 3 hours. As the mold temperature increased the pressure rose to approximately 21 MPa. At this point some of the gases were released and the pressure dropped to about 13 MPa, which is still above the critical point. (This step demonstrates that the press is capable of acting as a pressure-relief valve when the internal pressure gets too high.) After about a 15 minute soak, the press restraining force was dropped to 4 kN, allowing for evacuation of the supercritical gases and rapid dropping of the internal mold pressure to ambient pressure while maintaining a high temperature. In the final stage, the press was cooled down to ambient temperature in 1.5 h. FIG. 3 shows that the process successfully avoids crossing the methanol liquidus line.

The process is a one-step precursor to aerogel method. During processing, the specimen experiences the stages of gelation, aging/strengthening, solvent extraction, and cooling to ambient temperature. Gelation refers to the polymerization reaction that results in a solid network suspended in the liquid solvent. The specimen is said to have gelled when the polymer network has spanned all sides of the container, although the polymerization reactions continue as the products approach equilibrium compositions. The post-gelation polymerization is referred to as the aging and strengthening stage. In a separate gelation study, it has been demonstrated that gelation occurs in the first 120 minutes of the temperature ramp phase. During the remaining 75 min of the ramp and during the upper-temperature soak, the gel has a chance to strengthen and age. Although thermal stresses are a primary concern in setting the temperature ramp rate, the process must allow sufficient time for the gelation and aging/strengthening stages.

The processing cycle eliminates the capillary forces that cause fracture by avoiding liquid-gaseous interfaces. This control is achieved by staying on the liquid side of the methanol liquidus curve until the critical temperature and pressure are reached (as shown in FIG. 3). As a supercritical fluid, the processing curve can go around the liquidus curve (without crossing it) to ensure that the removal of the liquid phase does not take place in the presence of a gas phase.

During the high-temperature soak step of the process, the system is brought to a supercritical temperature and held there to ensure that the entire specimen exceeds the critical temperature. At that point the restraining force on the hydraulic press is relaxed nearly instantaneously to a nominal load (4 kN). This nominal load is maintained to prevent air from entering the mold and oxidizing any remaining precursor chemicals while at high temperature. As the restraining force is released, the supercritical fluid escapes through newly formed gaps between the gasket and the mold. It is important to the design of the mold gasket assembly that the fluid remains completely trapped under the restraining force, yet escapes relatively easily during the relaxation. For example, the process described above utilizes Kapton film to prevent the gasket material from adhering to the platen and mold. After the extraction, the aerogel is formed, but remains inside the mold at an elevated temperature. At this point the solvent has been evacuated and the cooling path is no longer constrained by the liquidus curve. Thermal stresses are less problematic during the cooling stage because the network has already formed and the solvent has been evacuated. At present, the cooling rate is limited by the capabilities of the hot-press.

The new fabrication technique has proven to be a successful method for fabricating silica aerogel monoliths, forming aerogels in about 5 hours with thermo-physical properties that are comparable to those of aerogels made using prior techniques.

Example 3

Characterization of Aerogels

Figure 4A:
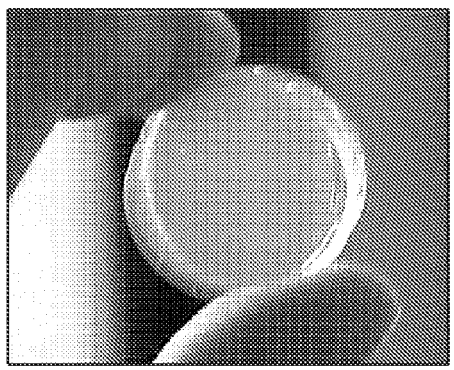
FIGS. 4A-B illustrate two aerogel monoliths produced by the method of the present invention. The monolith shown in FIG. 4A is about 25.4 mm diameter×12.5 mm high. The monolith shown in FIG. 4B is about 24 mm diameter×17 mm high.
Figure 4B:
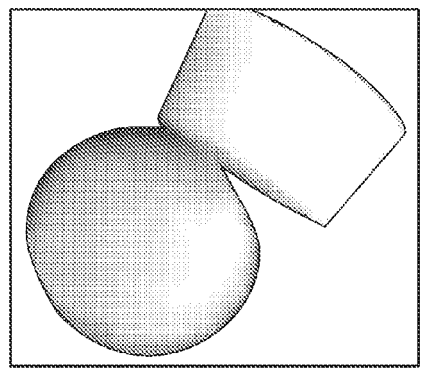

Using the procedure described in Example 2, several monolithic cylindrical aerogel samples were prepared. Sample aerogel monoliths are shown in FIGS. 4A-B.

Bulk density measurements were made using a caliper and mass balance. Values as low as 0.066 g.cm$^{-3}$ were measured.

Figure 5:
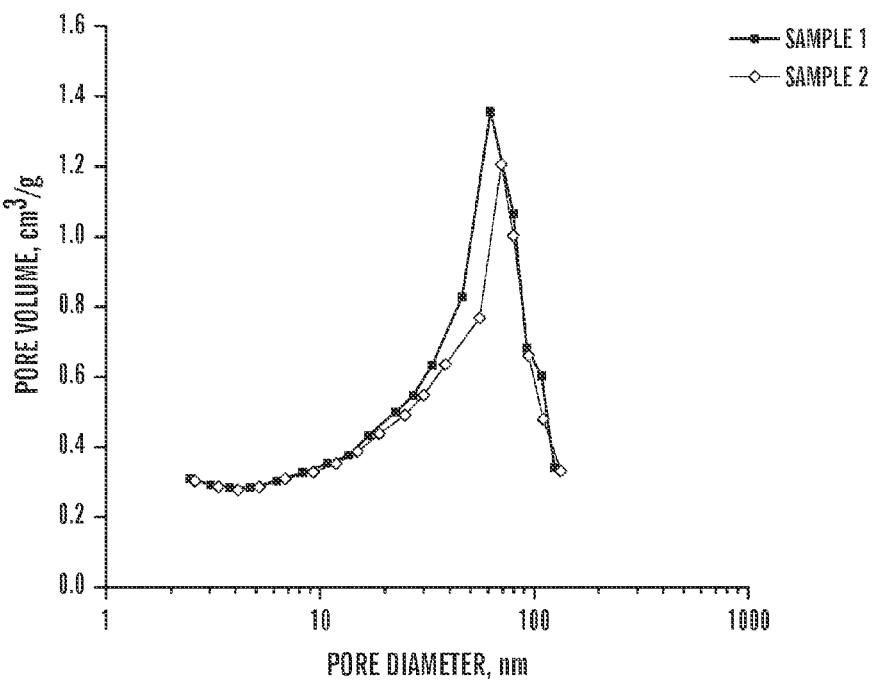
FIG. 5 is a graph illustrating the Barrett-Joyner-Halenda ("BJH") Desorption dV/dlogD pore-volume data for two sample aerogels fabricated in accordance with the present invention. The solid lines are used to visually connect the data and do not represent an analytical relation between pore diameter and pore volume.

The aerogel pore-size data were characterized using a Micromeritics ASAP 2010 Nitrogen Adsorption system (Micromeritics Instrument Corporation). Samples were outgassed for 5 hours at 200° C. prior to analysis. A 5-point Brunauer-Emmett-Teller (BET) analysis was used to determine surface area. Mesopore distributions were determined from the desorption branch of the nitrogen isotherm using the Barrett-Joyner-Halenda (BJH) method. The BET surface areas were found to be 320 m$^2$.g$^{-1}$, and the BJH desorption average pore size was found to be about 15 nm. Incremental pore volume was found to peak at 68 nm. FIG. 5 presents the desorption pore-size distribution. The 320 m$^2$.g$^{-1}$ surface area is relatively low for an aerogel. Poco et al. (*Mat. Res. Soc. Symp.* 431:297 (1996), which is hereby incorporated by reference in its entirety) also report low BET surface areas (compared to CSCE aerogels) for their RSCE aerogels. They attribute this to the accelerated gelation phase, which occurs at high temperatures in the RSCE process and may cause larger necks between particles.

A Hot Disk Thermal Constants Analyzer (HD-01) was used to perform aerogel thermal conductivity measurements. This system sensor is sandwiched between two pieces of aerogel material and heated by an electric current for a short period of time. The temperature response of the sensor is recorded and the transient record is analyzed to determine thermal properties. The tested aerogel samples had conductivity values between 30 and 40 mW.mK$^{-1}$.

Figure 6:
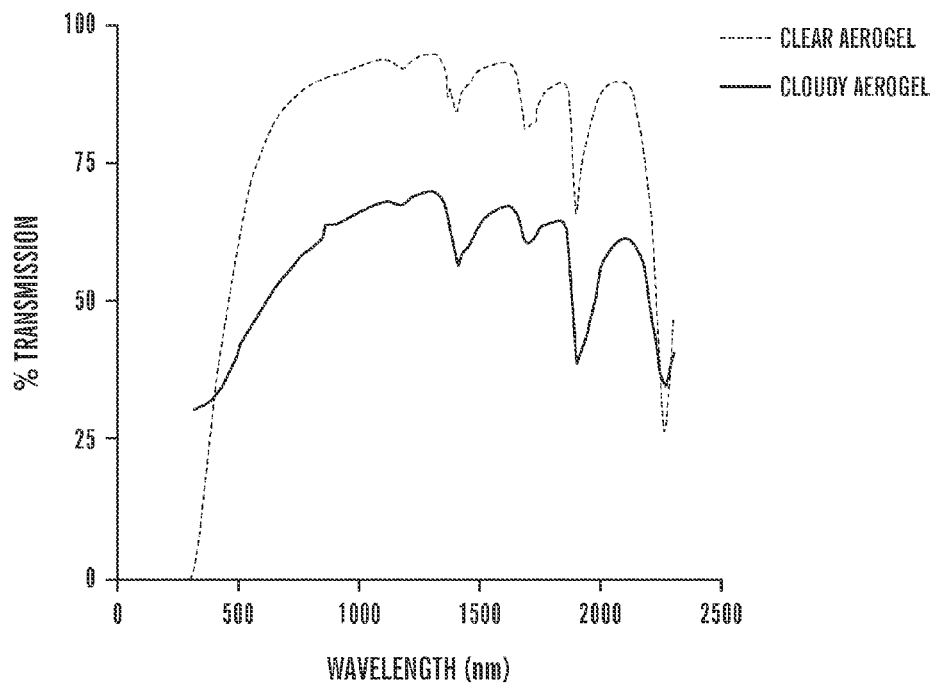
FIG. 6 is a graph illustrating the transmission results as a function of wavelength of light for two aerogel samples, which both show transmission of 60-90% in the near-infrared region.

A Perkin-Elmer Lambda 900 Series spectrophotometer was used to perform the transmission measurements in the 300 to 2500 nm range. The transmission results are presented in FIG. 6 for two aerogel samples. Although both samples were prepared using the same process, one of the samples was cloudy and had low transmissivity in the visible range. Both samples transmitted 60-90% of the light at near-infrared wavelengths (1200 to 2200 nm). Peaks observed in the near-infrared region are characteristic of silica sol-gels and agree well with the literature (Venkateswara et al., *Mater. Sci. Technol.* 14:1194 (1998), which is hereby incorporated by reference in its entirety). Transmission in the visible region is limited (particularly for the cloudy sample) due to Rayleigh scattering, which is particularly significant at lower wavelengths. As noted in Example 7 infra, the aerogels transmit sufficiently in the visible region to be used as platforms for optical sensors based on entrapped fluorescent probes.

Example 4

Fabrication of Aerogels

Figure 7A:
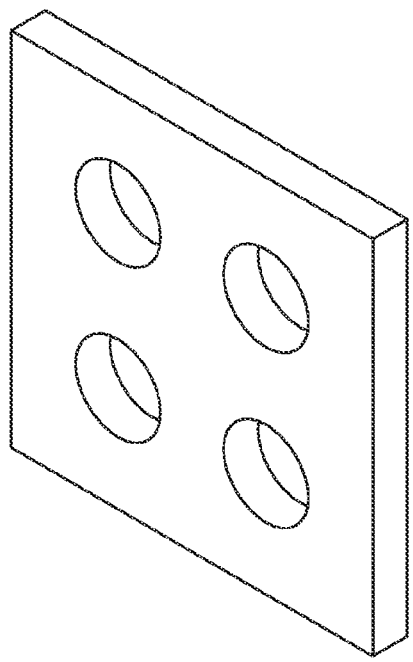
FIGS. 7A-C illustrate different mold constructions that have been used to prepare aerogels using the process of the present invention.

In this example, four 1.5 inch diameter×¾ inch high silica aerogels were prepared using the mold illustrated in FIG. 7A. The mold was sandwiched between two pieces of sealing material (¹⁄₁₆ inch thick graphite sandwiched between 2 mil thick pieces of Kapton film) and placed in the hot press, which was then closed and held with a restraining force of 35 kN (8,000 lb) for two minutes to seal the bottom of the mold.

A 110 ml batch of precursor solution was prepared using 23.43 ml of TMOS (>98%), 75.58 ml of pure methanol, 10.63 ml of de-ionized water and 0.37 ml of 1.5M NH$_4$OH. The ingredients were mixed and briefly stirred.

The press was then opened, the upper sealing material removed, and the precursor solution was distributed among the four holes. The upper sealing material was placed back on the mold and the press was closed. The restraining force was set to 180 kN (40,400 lb), and the temperature was increased to 288° C. (550° F.) at a rate of 1.2° C./min (2.2° F./min). Upon reaching 288° C. (550° F.), the mold remained at this temperature for 2 hours.

After two hours, the restraining force was dropped to 26 kN (5775 lb) at a rate of 5.1 kN/min (1150 lb/min). The mold remained at 288° C. (550° F.) and 26 kN (5775 lb) for 2 hours, after which the temperature was decreased from 288° C. to 38° C. at a rate of 1.2° C./min. After reaching 38° C., the press was opened and the four aerogels were removed.

Example 5

Fabrication of Aerogels

Figure 7B:
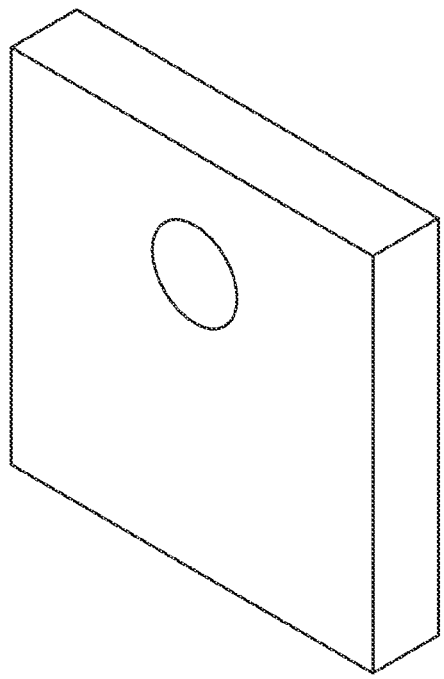

In this example, a ¾ inch diameter×1 inch high silica aerogel was prepared using the mold illustrated in FIG. 7B. The mold was sandwiched between two pieces of sealing material (1/16 inch thick graphite sandwiched between 2 mil thick pieces of Kapton film) and placed in the hot press, which was then closed and held with a restraining force of 35 kN (8,000 lb) for two minutes to seal the bottom of the mold.

A 10 ml batch of precursor solution was prepared using 2.125 ml of TMOS (>98%), 6.875 ml of pure methanol, 0.90 ml of de-ionized water, and 0.034 ml of 1.5M $NH_4OH$. The ingredients were mixed and briefly stirred.

The press was then opened, the upper sealing material removed, and the precursor solution poured into the hole. The upper sealing material was placed back on the mold and the press was closed. The restraining force was set to 74 kN (17,000 lb), and the temperature was increased to 288° C. (550° F.) at a rate of 1.2° C./min (2.2° F./min). Upon reaching 288° C. (550° F.), the mold remained at this temperature for 2 hours.

After two hours the restraining force was dropped to 26 kN (5775 lb) at a rate of 1.6 kN/min (364 lb/min). The mold remained at 288° C. and 26 kN for 2 hours, after which the temperature was decreased from 288° C. to 38° C. at a rate of 1.2° C./min. After reaching 38° C., the press was opened and the single aerogel was removed.

Example 6

Preparation of Probe-Doped Aerogels

Tetramethoxysilane (TMOS) was purchased from Sigma-Aldrich at 98% purity. Solutions of the $[Ru(bpy)_3]Cl_2.6H_2O$ dye (Strem Chemicals, 98% purity) were prepared in deionized water. Solutions of the $[Ru(dpp)_3]Cl_2.6H_2O$ dye (GFS Chemicals, unlisted purity) were prepared using absolute ethanol ($CH_3CH_2OH$, EtOH), unless otherwise noted. The PtOEP was purchased from Frontier Scientific. Spectrometric grade methanol was purchased from Aldrich.

The $[Ru(dp_P)_3]Cl_2.6H_2O$ solid was purified by washing with chilled, distilled deionized water using fine-grade filter paper (Fisher Scientific), as suggested by Cho and Bright (*Anal. Chem.* 73: 3289-3293 (2001), which is hereby incorporated by reference in its entirety). After drying under ambient conditions, 0.0117 g of $[Ru(dpp)_3]Cl_2.6H_2O$ was dissolved in 10.0 ml of absolute EtOH to make a $1.0 \times 10^{-3}$ M $Ru(dpp)_3^{2+}$ stock solution. Additional EtOH solutions of varying $Ru(dpp)_3^{2+}$ concentration, ranging from $2.5 \times 10^{-7}$ to $1.0 \times 10^{-4}$ M, were prepared by dilution of the stock solution.

A saturated solution of PtOEP in methanol was prepared by placing 5 mg of PtOEP powder into a 100 ml volumetric flask, which was then filled to the mark with methanol. (Not all of the powder dissolved, as PtOEP is not very soluble in methanol.) In preparing sol-gels, 10.00 ml of the PtOEP stock solution was used.

Figure 7C:
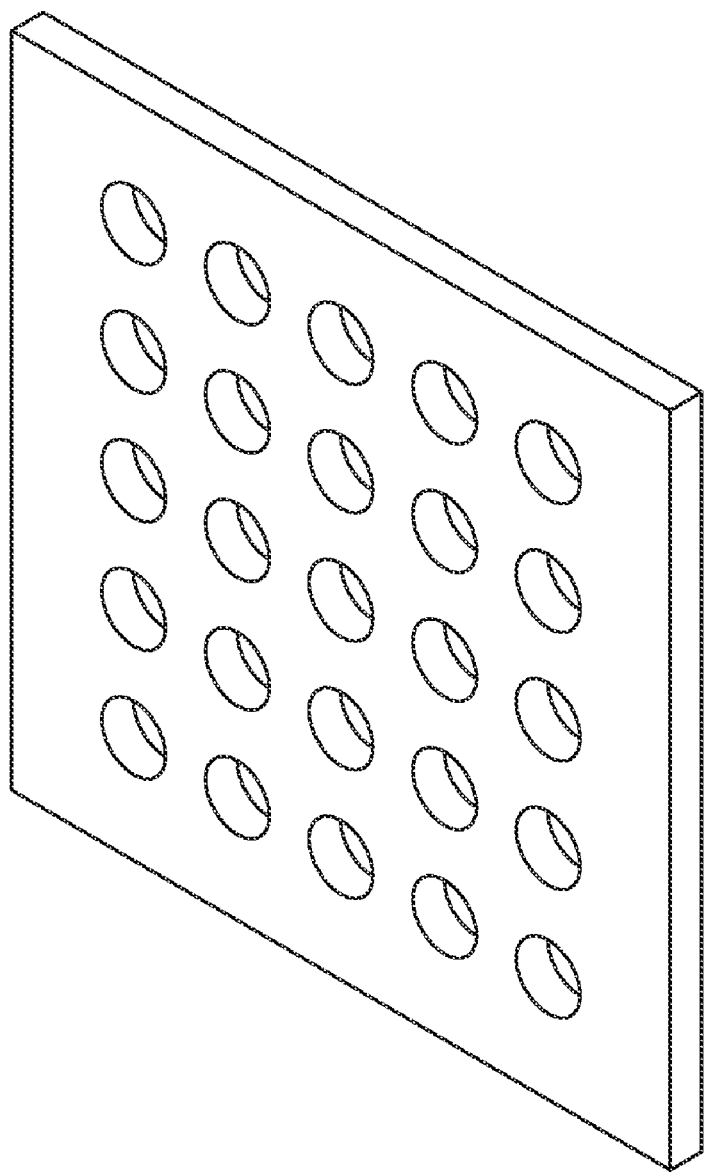
Figure 8A:
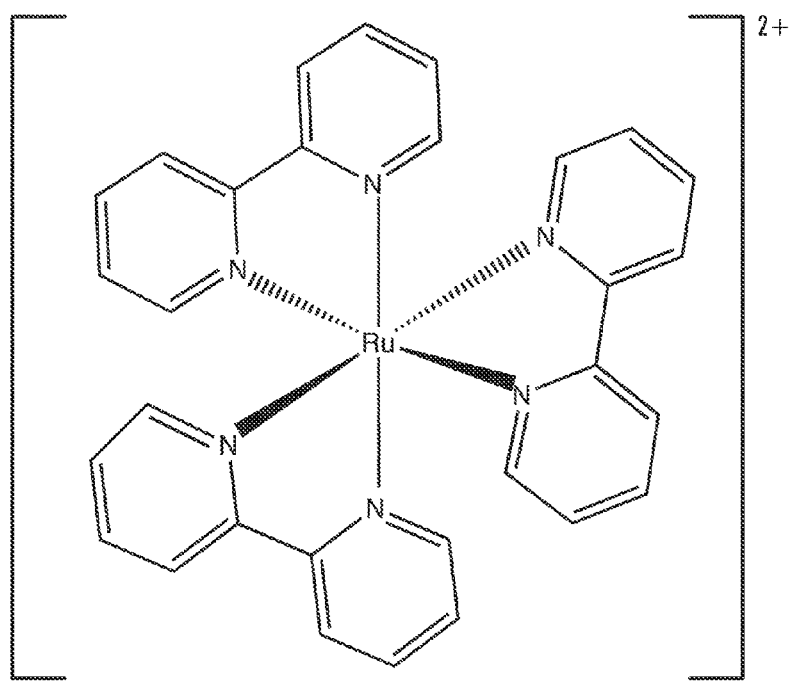
FIGS. 8A-C illustrate the structures of oxygen-sensitive probes used in Example 6.
Figure 8B:
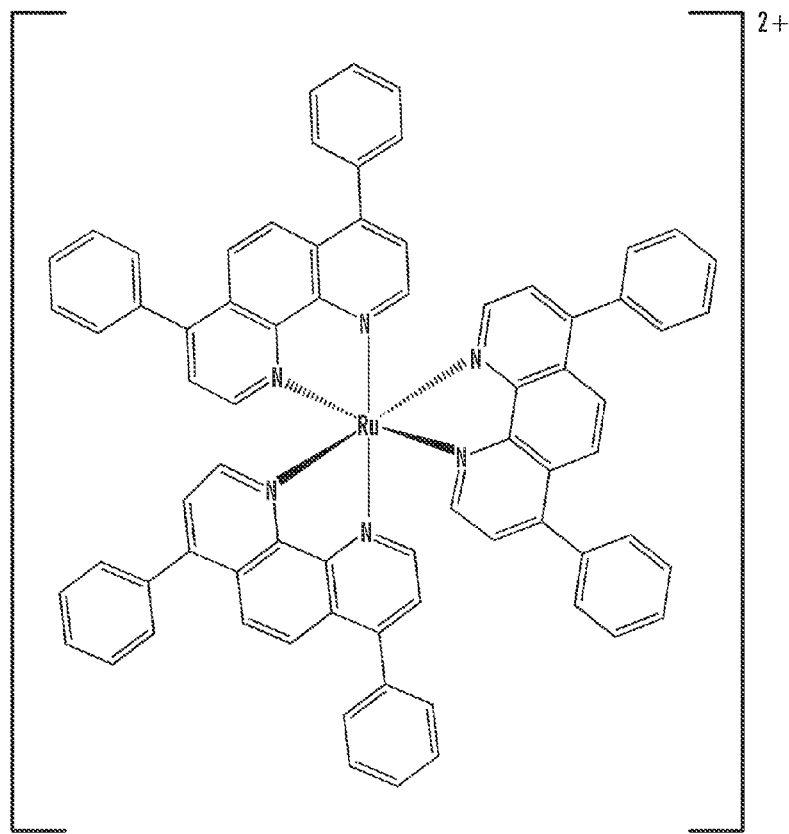
Figure 8C:
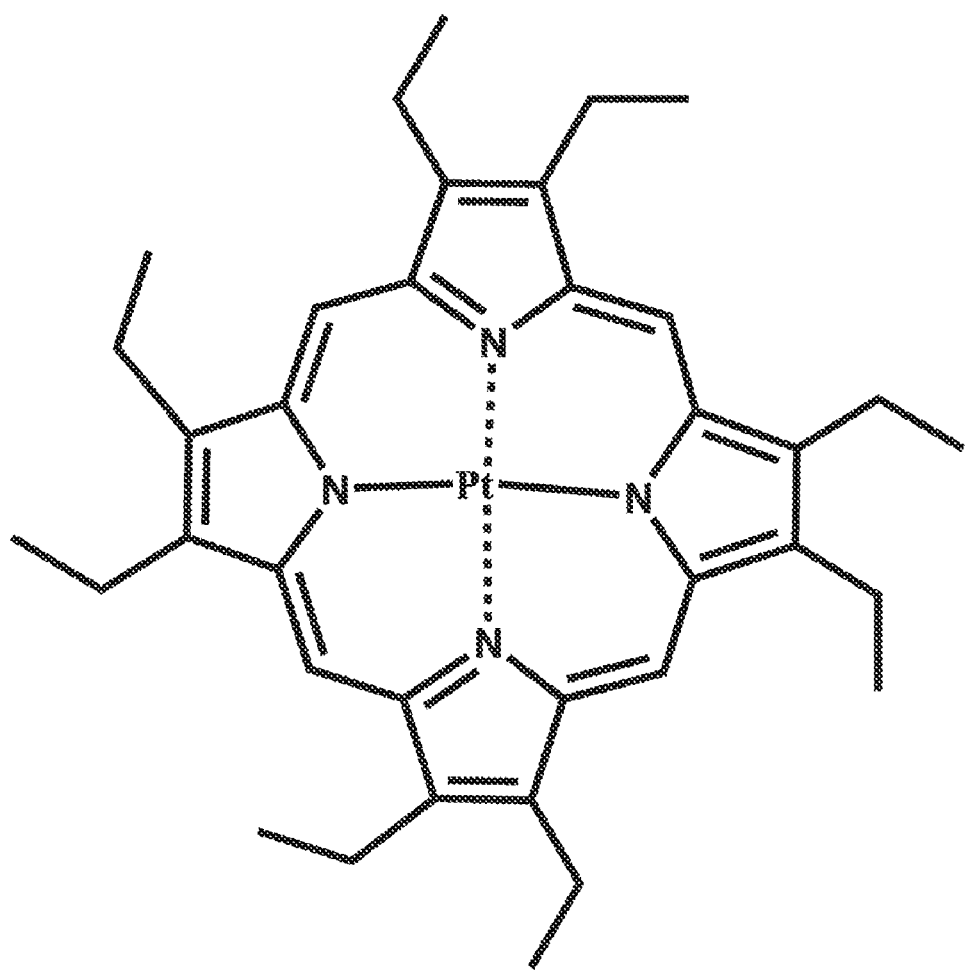

To prepare the sol-gels, TMOS (4.24 ml), methanol (13.70 ml), deionized water (2.10 mL), and 1.5 M aq. ammonia (0.067 ml) were combined and the solution stirred until it was monophasic (~10 min). Probes were introduced as a volume of aqueous solution, in place of a portion of the water, or as an alcohol solution, in place of a portion of the methanol. The sol-gel-precursor solution was then either (1) poured into disposable polystyrene cuvettes for xerogel preparation under ambient conditions, or (2) poured into a metal mold (see FIG. 7C) and placed into a hot press for aerogel preparation using a procedure of the type described in Example 5 supra.

Example 7

Spectroscopic Characterization of Probe-Doped Aerogels

A PTI Steady State Fluorometer System, containing a PTI A-1010 Arc Lamp, a PTI LPS-220B Lamp Power Supply, and a PTI Model 810/814 Photomultiplier Detection System, was used to take fluorescence excitation and corrected emission spectra, and to collect time-based emission scans used in gas sensor experiments. A Hewlett Packard model HP8453 Diode Array spectrophotometer was used to take absorbance measurements of the stock solutions and doped sol-gels.

The PTI Steady State Fluorometer System described above was used to calibrate the response of the doped sol-gels to ambient oxygen concentration. All measurements were obtained at a fixed excitation and emission wavelength appropriate to the probe.

For the initial sensor response experiments, the sample's fluorescence intensity was monitored continuously while the sample (in a cuvette) was alternately exposed to ambient conditions (room air) and flushed with nitrogen from an ultrapure nitrogen gas tank. This method was simple, but it was not suitable for quantitative studies; moreover, the gas pressure on the sample was not carefully regulated, and the resulting changes in pressure on the samples as the nitrogen tank was turned on and off caused some of the sol-gels to move in the excitation beam. This variable motion was a particular problem for the xerogels, which had shrunk considerably since gelation.

Subsequently, a gas-mixing system depicted in FIG. 9 was constructed. The ambient oxygen content was controlled by mixing ultrapure air and $N_2$ (g) using a 150 mm Airgas Gas Proportioner. The second-stage regulators were set to 20 psi for both $N_2$ (g) and air. The line regulator was opened maximally and gave a reading of 17.5 psi. The flow rate into the cuvette was calculated to be 1800±30 mL/min, using the manufacturer's calibration data for the gas proportioner. A cuvette cap was modified for transport of the gas mixture to and from the sample, as depicted in FIG. 9C.

Immediate success was achieved in entrapping these probes in both aerogels and xerogels prepared using TMOS. Unbroken cylindrical aerogel monoliths, ~1 cm in diameter and 1.5 cm in height, containing each of the three probes were obtained via the procedure of the present invention. The aerogels appear cloudier than xerogels, indicating a significant amount of light is being scattered; however, the aerogel monoliths are sufficiently transparent that no difficulty was encountered in taking fluorescence measurements.

When $Ru(bpy)_3^{2+}$ solutions of $1.0 \times 10^{-5}$, $1.0 \times 10^{-4}$, and $1.0 \times 10^{-3}$ M were used in the sol-gel recipe, optically transparent aerogels were produced. Higher concentrations yielded opaque aerogels; lower concentrations did not give sufficient fluorescence intensity for spectral measurements. Aerogels and xerogels prepared with $Ru(dpp)_3^{2+}$ stock solutions of $1.0 \times 10^{-5}$ and $1.0 \times 10^{-4}$ M yielded optically usable monoliths. Undissolved solid PtOEP precipitated out of the PtOEP-doped sol-gels during the gelation process. The PtOEP precipitate is visible at the base of the monoliths, but this area is not probed during the spectroscopic measurements.

High-quality absorption spectra of the doped aerogels could not be obtained, because they scattered too much light. Excitation spectra for the $Ru(bpy)_3^{2+}$-doped xerogels and aerogels peaked at 470 nm. The emission maxima for the aerogels was red-shifted from that of the same probe in xerogels: 598-604 nm for various aerogels versus 590 nm for the xerogels.

The fluorescence spectral properties of $Ru(dpp)_3^{2+}$ in xerogels and aerogels somewhat depended on fluorophore concentration. The emission spectrum of the aerogel prepared from $1.0 \times 10^{-5}$ M $Ru(dpp)_3^{2+}$ solution had a peak at 602 nm, blue-shifted relative to the 615 nm peak observed for the complex in ethanol. This wavelength is fully consistent with the corresponding $Ru(dpp)_3^{2+}$-doped xerogel. Hence, it is possible that the environment(s) experienced by the probe in the xerogel and the aerogel are very similar for these samples.

The UV-visible absorption spectra of the PtOEP stock solution (in methanol) and wet gels were consistent with the literature (Lee et al., *Analyst* 122:81 (1997), which is hereby incorporated by reference in its entirety). Emission spectra of PtOEP in solution, in aerogels, and in xerogels showed maxima at 646 nm with no significant differences in maximum emission wavelength. The PtOEP-doped xerogels fluoresced appreciably only in the absence of $O_2$.

Figure 10:
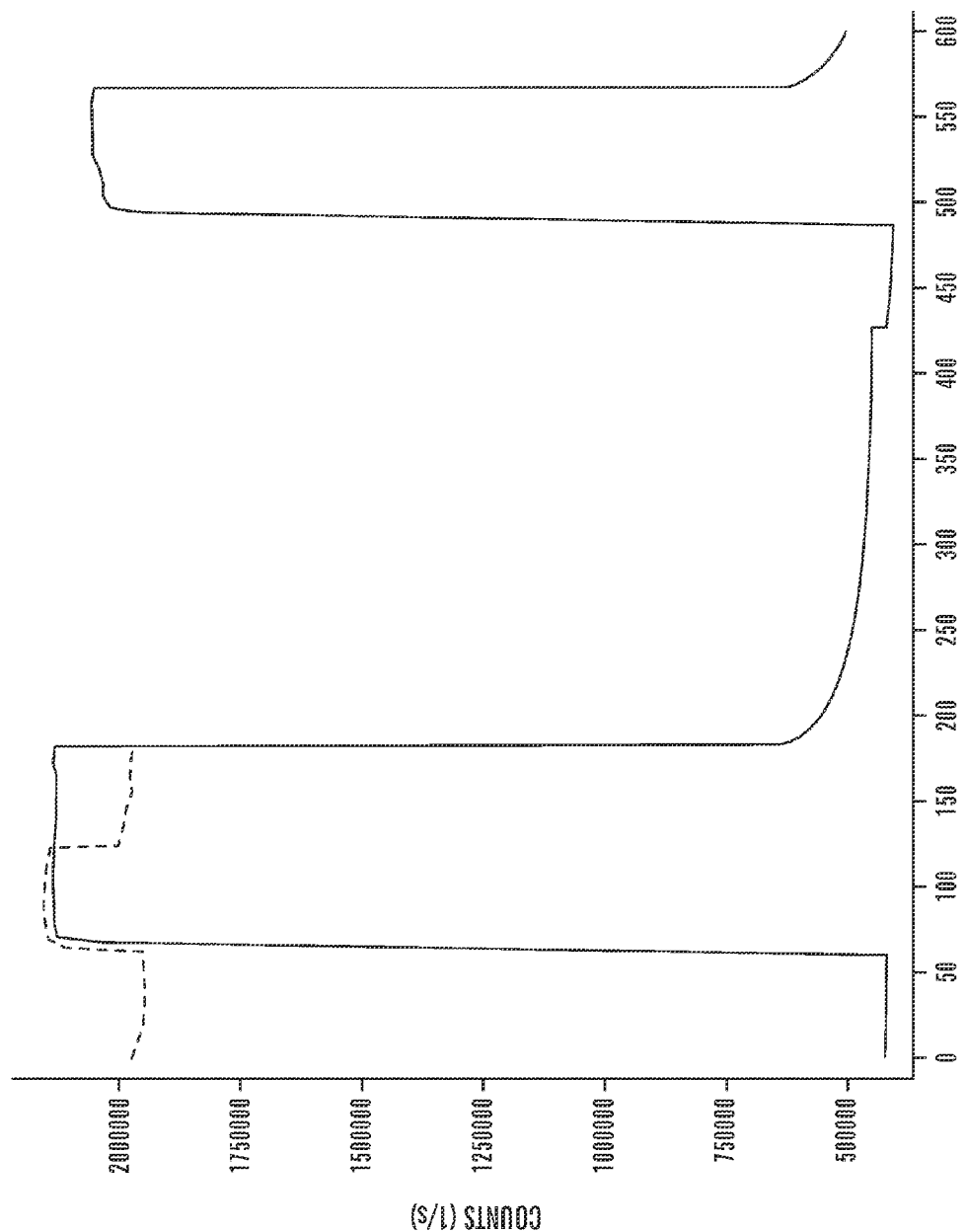
FIG. 10 is a graph illustrating the reversible response of $Ru(bpy)_3^{2+}$- and $Ru(dpp)_3^{2+}$-doped aerogels to changes in ambient $O_2$ (g) concentration. The response of the $Ru(bpy)_3^{2+}$-doped aerogel was normalized to that of the $Ru(dpp)_3^{2+}$-doped aerogel. Each sample was initially in air under ambient conditions in an uncapped cuvette. At approximately t=60 s, $N_2$ (g) was allowed to impinge directly onto the sample. The $N_2$ (g) was then shut off at 120 s (a) and 180 s (b only). An additional cycle is shown in run (b). $\lambda_{ex}$=446 nm, $\lambda_{em}$=615 nm, 10 data pts/s.
Figure 11:
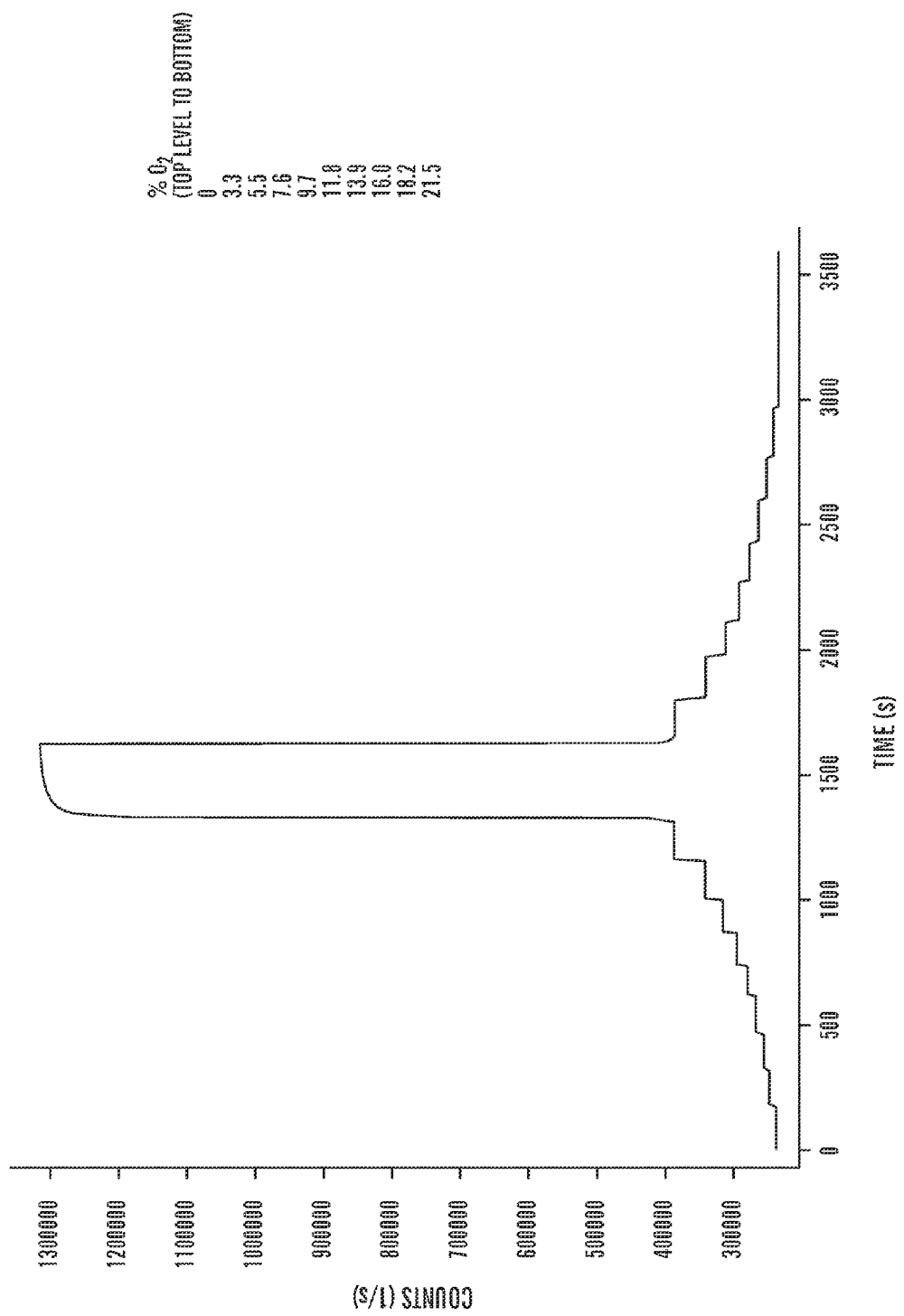
FIG. 11 is a graph that illustrates a time-based scan showing response to oxygen and reversibility of $Ru(dpp)_3^{2+}$-doped silica aerogel sensor. Each step represents a certain percentage of oxygen. The scan was taken using $\lambda_{ex}$=446 and $\lambda_{em}$=615 nm.

When a $Ru(bpy)_3^{2+}$-doped aerogel was exposed to 100% nitrogen, the fluorescence intensity of the entrapped $Ru(bpy)_3^{2+}$ underwent a rapid increase of ~10%, with the signal stabilizing within 10 s (see FIG. 10). The signal was reversible. The $Ru(dpp)_3^{2+}$-doped aerogels gave considerably greater relative response to changes in the percentage oxygen than those doped with $Ru(bpy)_3^{2+}$, as can be seen in FIG. 10. Consequently, these samples were explored in greater detail. FIG. 11 displays a time-based emission scan of a $Ru(dpp)_3^{2+}$-doped aerogel. The sample showed a quick and reversible response time (<10 s) to the analyte (oxygen).

Each 'step' in this scan represents the fluorescence emission intensity of the doped aerogel at a certain oxygen percentage. For example, the step between 0 and ca. 175 s represents the emission of the dye-doped aerogel when exposed to 21.5% oxygen. The $O_2$ (g) concentration was first decreased from 21.5% to 0% $O_2$ (g) while monitoring the signal intensity; and then increased stepwise to 21.5% while again monitoring. The response was reversible and exhibited strong reproducibility: when the average emissions for each percentage step-up and step-down in $O_2$ are plotted together, the data points are superimposable within one standard deviation. The fluorescence intensity of the doped aerogel in 100% nitrogen is a factor of 5.4 times greater than when the same sensor is exposed to 21.5% oxygen. However, the $Ru(dpp)_3^{2+}$-doped aerogel does not respond to changes in ambient $O_2$ (g) concentration in a linear fashion.

The $Ru(dpp)_3^{2+}$-doped aerogel was highly sensitive to low $O_2$ (g) concentrations, with the signal intensity dropping to less than one-third of its maximum when going from 0 to 3% $O_2$ (g). The signal response of a $1.0 \times 10^{-4}$ M $Ru(dpp)_3^{2+}$-doped xerogel was also tested for changes in ambient oxygen concentration. After applying a positive pressure of $N_2$ (g), the xerogel signal responded fully and stably after 50 s, with a 7.25-fold signal increase. This response was also shown to be reversible. It is important to note that the 50 s response time was obtained with a much lower $N_2$ (g) flow rate than was used for the $Ru(dpp)_3^{2+}$-doped aerogel, because the xerogel sample physically moved out of the excitation beam when higher flow rates (~1800 ml.min$^{-1}$) were employed. Response times for the xerogel that was post-doped with $Ru(dpp)_3^{2+}$ were similar; however, a greater relative change in fluorescence intensity (factor of 8.6) was observed. For purposes of comparison, it should be noted that the $5.0 \times 10^{-6}$ M $Ru(dpp)_3^{2+}$ solution exhibited a 6.3-fold increase in fluorescence intensity after it was vigorously bubbled with $N_2$ (g); however, 69 min of deaeration was required to produce a steady response.

Figure 12:
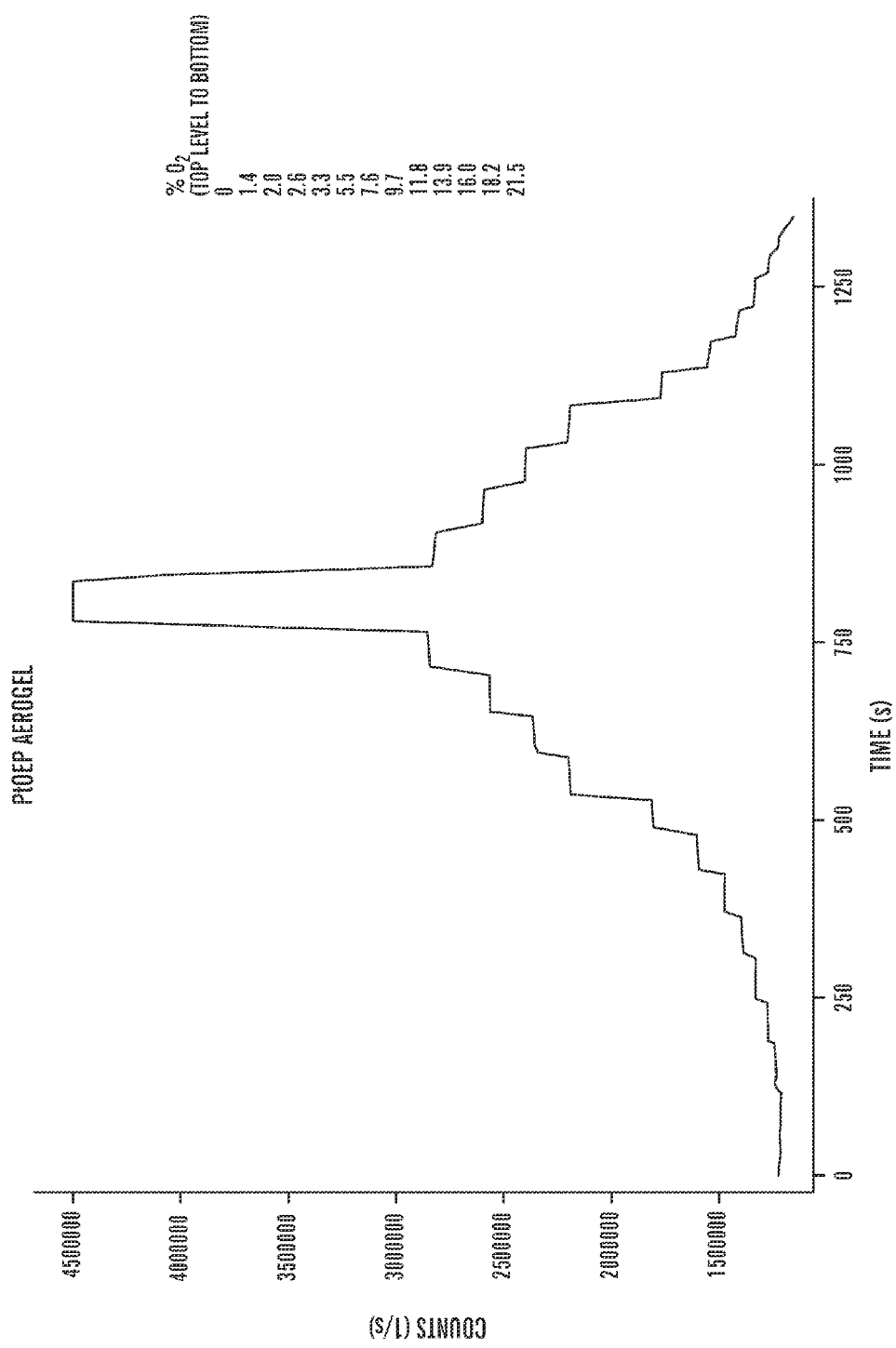
FIG. 12 is a graph that illustrates a time-based scan showing response to oxygen and reversibility of PtOEP-doped silica aerogel sensor. Each step represents a certain percentage of oxygen. The scan was taken using $\lambda_{ex}$=533 and $\lambda_{em}$=646 nm.

The PtOEP-doped aerogel responded to oxygen concentration with a response time to increases in oxygen concentration of ~20 s. When decreasing the oxygen concentration, stabilization of the signal was achieved in about 10 s. FIG. 12 is a time-based scan of the PtOEP-doped aerogel; it demonstrates the response of the doped aerogel to its gaseous environment.

Time-based scans of PtOEP-doped xerogels using the same gas mixes demonstrated that the xerogels were not sensitive to changes in oxygen percentages ranging from 21.5 to 1.4%. Fluorescence emission of the xerogel changed significantly (by a factor of 1.8) when in the complete absence of oxygen.

Quenching processes decrease the emission intensity of fluorescent species. In collisional (dynamic) quenching, the excited fluorophore transfers its excess energy via non-radiative pathways to a quencher before it has the opportunity to emit a photon via fluorescence. Oxygen is an efficient collisional quencher, diffusing to the fluorophore during the lifetime of the excited state (Lakowicz, *Principles of Fluorescence Spectroscopy*, 2nd Ed., Kluwer Academic/Plenum Publishers (1999), which is hereby incorporated by reference in its entirety).

The Stern-Volmer equation (shown below) can be used to generate calibration curves (Lakowicz, *Principles of Fluorescence Spectroscopy*, 2nd Ed., Kluwer Academic/Plenum Publishers (1999), which is hereby incorporated by reference in its entirety).

$$F_o/F = 1 + K_{SV}[Q] \qquad \text{Eq. (2)}$$

where $F_o$ is the fluorescence of a species in the absence of quencher; F is the fluorescence of that species in the presence of quencher; [Q] is the concentration of the quencher; and $K_{SV}$ is the Stern-Volmer quenching constant. A Stern-Volmer plot, $F_o/F$ v. [Q], is linear if the fluorophore is present in a single microenvironment. A nonlinear Stern-Volmer plot can indicate that the fluorophore has partitioned into different environments with different quencher accessibilities (Lakowicz, *Principles of Fluorescence Spectroscopy*, 2nd Ed., Kluwer Academic/Plenum Publishers (1999), which is hereby incorporated by reference in its entirety).

Figure 13:
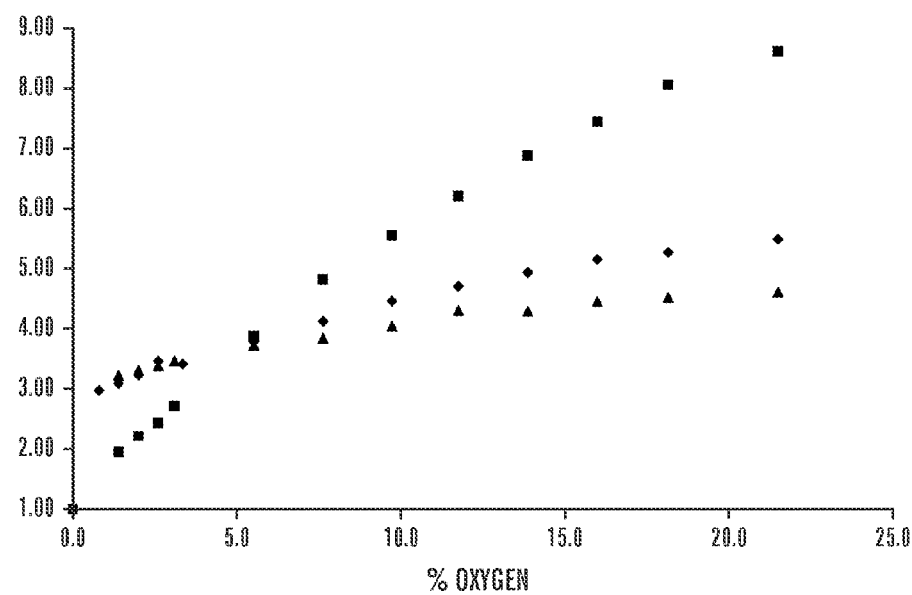
FIG. 13 is a graph illustrating Stern-Volmer plots for $Ru(dpp)_3^{2+}$-doped silica aerogel (♦), xerogel (▲), and post-doped xerogel (■).

Calibration curves for the more promising sensor materials were produced using the Stern-Volmer Eq. (1). FIG. 13 shows the Stern-Volmer plots for the $Ru(dpp)_3^{2+}$-doped materials: an aerogel, a xerogel, and a post-doped xerogel. For the aerogel and xerogel, it is clear that the plots of $F_o/F$ vs. % $O_2$ are not linear, even at low % $O_2$. Hence, the oxygen-sensitive $Ru(dpp)_3^{2+}$ is present in at least two different microenvironments with differing oxygen accessibility. The Stern-Volmer plot of the post-doped xerogel has increased linearity when compared to the aerogel and the xerogel prepared by adding to the precursor mixture prior to gelation.

Figure 14:
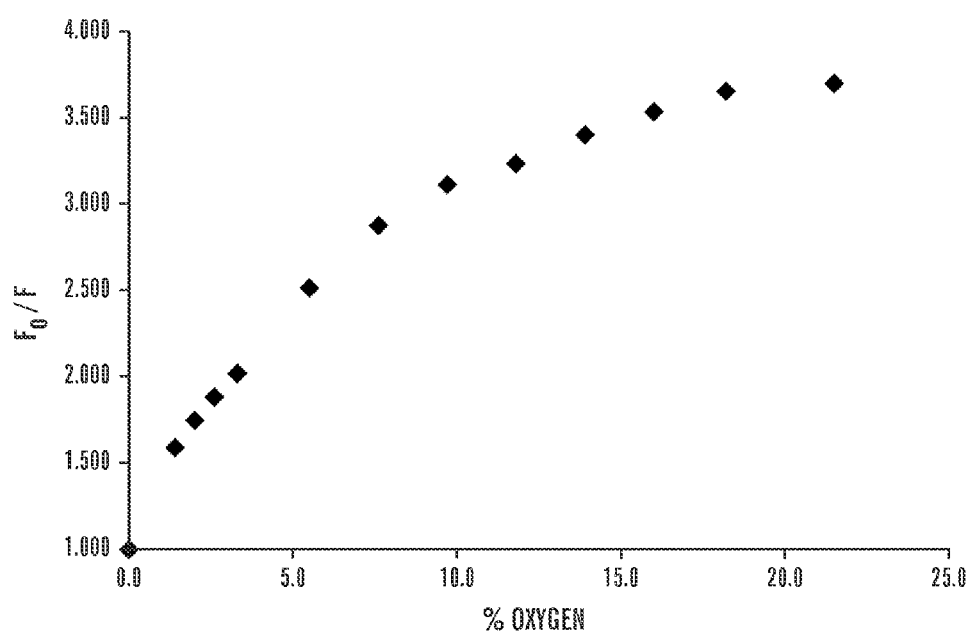
FIG. 14 is a graph illustrating a Stern-Volmer plot for PtOEP-doped aerogel.

A Stern-Volmer plot of the PtOEP-doped aerogel data (FIG. 14) indicates that the response of the sensor is approximately linear for the 0.0% to 5.5% $O_2$ range. At higher % $O_2$, it becomes obvious that the Stern-Volmer plot is not linear, indicating that PtOEP is present in at least two microenvironments within the aerogel.

As a result of multi-site binding, nonlinear Stern-Volmer plots are common for sol-gel-based sensors (Leventis et al., *Chem. Mater.* 16:1493 (2004); Watkins et al., *Appl. Spectrosc.* 52:750 (1998); Baker et al., *J. Sol-Gel Sci. Technol.* 17:71 (2000); Tang et al., *Anal. Chem.* 75:2407 (2003), each of which is hereby incorporated by reference in its entirety). A two-site quenching model developed by Demas et al. (*Anal. Chem.* 67: 1377 (1995), which is hereby incorporated by reference in its entirety) was employed in modeling this data. If a single sensor species exists in two sites, each with a different quenching constant, the following relationship applies:

$$\frac{F_0}{F} = \frac{1}{\frac{f_{01}}{1+K_{SV1}[Q]} + \frac{f_{02}}{1+K_{SV2}[Q]}} \qquad \text{Eq. (3)}$$

where $F_{01}$ and $f_{02}$ are the fractional contributions of the probe in each site to the unquenched steady-state emission ($f_{01} + f_{02} = 1$); $K_{SV1}$ and $K_{SV2}$ are the quenching constants for the two different sites (Demas et al., *Anal. Chem.* 67: 1377 (1995), which is hereby incorporated by reference in its entirety). The program Kaleidagraph was used to fit the data presented in FIGS. 12 and 13 (Stern-Volmer plots for the fluorophore-doped materials) to the two-site quenching model. In all cases, very good fits were obtained ($R^2 = 0.992$). The parameters obtained from the curve-fits are listed in Table 1 below.

methanol, it will increase the number of viable probes. Moreover, the high temperatures required for aerogel formation via the process of the present invention might be advantageous in certain cases. For instance, Baker et al. demonstrated that $Ru(dpp)_3^{2+}$-doped sol-gel thin films cured at relatively higher temperatures (>150° C.) were more sensitive to oxygen than films prepared at lower temperatures (*J. Sol-Gel Sci. Technol.* 17:71 (2000), which is hereby incorporated by reference in its entirety). This effect was due, in part, to the dissociation of water from residual silanol groups in the sol-gel at higher temperatures (Baker et al., *J. Sol-Gel Sci. Technol.* 17:71 (2000), which is hereby incorporated by reference in its entirety).

The porous silica aerogels prepared by the process of the present invention made excellent platforms for gas sensors. The three tested oxygen-sensitive species each maintained sensitivity to oxygen when immobilized in TMOS-based aerogel monoliths. Oxygen diffused rapidly through the aerogel matrix, and interacted with entrapped indicators. Response times were comparable to those observed by Leventis et al. for a covalently attached probe (Leventis et al., *Chem. Mater.* 11:2837 (1999), which is hereby incorporated by reference in its entirety) and for an aerogel post-doped with a ruthenium complex (Leventis et al., *Chem. Mater.* 16:1493 (2004), which is hereby incorporated by reference in its entirety). Because the gas mixing system described above required manual adjustment of the $N_2$ (g) and air proportions, response times reported herein are likely longer than the actual response of the sensor.

It is likely that some probes will be immobilized in a sufficiently rigid manner so as to render them unsuitable as indicators for gas-phase analytes in sensor applications. Indeed, the relatively small change in signal (as shown in FIG. 10) limits the practical applicability of the $Ru(bpy)_3^{2+}$-doped

TABLE 1

Effect of matrix on the oxygen quenching of probe-doped materials

|  | $Ru(dpp)_3^{2+}$-doped Aerogel | $Ru(dpp)_3^{2+}$-doped Xerogel | Post-doped $Ru(dpp)_3^{2+}$ Xerogel | PtOEP-doped Aerogel |
|---|---|---|---|---|
| $f_{01}$ | 0.30 ± 0.01 | 0.050 ± 0.007 | 0.274 ± 0.008 | 0.18 ± 0.01 |
| $K_{SV1}$ (% $O_2$)$^{-1}$ | 0.033 ± 0.003 | * −0.003 ± 0.004 | 0.015 ± 0.002 | * −0.005 (± 0.002) |
| $f_{02}$ | 0.70 | 0.95 | 0.726 | 0.72 |
| $K_{SV2}$ (% $O_2$)$^{-1}$ | 14 ± 5 | 0.66 ± 0.02 | 10. ± 2 | 0.53 ± 0.03 |
| $R^2$ | 0.992 | 1.000 | 0.996 | 0.999 |

* = the value obtained from these fits indicates that the probe in one microenvironment is not significantly quenched by oxygen (i.e. $K_{SV1} \approx 0$); Note that values for $f_{02}$ were calculated by subtracting $f_{01}$ from 1.

As demonstrated above, aerogel-platform optical oxygen sensors can be prepared rapidly and inexpensively using the process of the present invention. The spectral data indicate small changes in the microenvironment experienced by the ruthenium complexes relative to solution, but there does not appear to have been significant degradation of the probes. It is important to note that the probes are exposed to high temperatures during the aerogel formation process, because the supercritical temperature of the methanol-water mixture must be reached in order for the solvents to be extracted from the sol-gel matrix. Thus, immobilization of thermally unstable probes is unlikely to be achieved.

For this initial demonstration of aerogel-platform gas sensors, species were selected that were expected to be relatively stable at the temperatures employed. If lower temperatures can be used or if the process can be optimized to reduce the amount of time spent above the supercritical temperature of aerogels as oxygen sensors. Preliminary fluorescence lifetime measurements indicate that there are two lifetimes for $Ru(bpy)_3^{2+}$ in the aerogel: one is unusually short (<5 ns) and does not change significantly as oxygen is removed from the aerogel; the other lifetime is approximately 770 ns in air, and 1580 ns in 100% nitrogen. The probe in the first microenvironment (with short lifetime) is, presumably, transferring energy to the silica matrix rapidly enough that oxygen quenching is not observed. Moreover, a substantial proportion of the probes within the aerogel matrix exhibit the shorter lifetime. We are continuing fundamental studies of the probe in these silica aerogels and the corresponding xerogels.

For the $Ru(dpp)_3^{2+}$-doped aerogels and xerogels, the dramatic increase in fluorescence intensity coincident with the removal of ambient $O_2$ (g) is consistent with the literature (Leventis et al., *Chem. Mater.* 16:1493 (2004); Watkins et al., *Appl. Spectrosc.* 52:750 (1998)); Baker et al., *J. Sol-Gel Sci.*

Technol. 17:71 (2000); Cho et al., *Anal. Chem.* 73:3289 (2001); Tang et al., *Anal. Chem.* 75:2407 (2003); Carraway et al., *Anal. Chem.* 63:337 (1991), each of which is hereby incorporated by reference in its entirety). This oxygen sensitivity makes $Ru(dpp)_3^{2+}$ an attractive probe for use as a gas sensor in an aerogel platform. However, the Stern-Volmer plots (FIG. 13) for the $Ru(dpp)_3^{2+}$-doped aerogels and corresponding xerogels indicate quite clearly that the $Ru(dpp)_3^{2+}$ probe exists in more than one microenvironment, each with differing accessibility to oxygen quenching. This behavior is consistent with previous work by Bright and coworkers (Watkins et al., *Appl. Spectrosc.* 52:750 (1998); Baker et al., *J. Sol-Gel Sci. Technol.* 17:71 (2000); Tang et al., *Anal. Chem.* 75:2407 (2003), each of which is hereby incorporated by reference in its entirety). When the data presented in FIG. 13 are fit to a two-site model (Table 1), it becomes clear that the microenvironments experienced by $Ru(dpp)_3^{2+}$ in the aerogel, xerogel, and post-doped xerogel differ.

When $Ru(dpp)_3^{2+}$ is entrapped in an aerogel or post-doped xerogel, it exists in at least two distinct microenvironments: ~30% of the signal in the absence of oxygen is due to the probe in an environment of low oxygen-sensitivity ($K_{SV1}$<0.05% $O_2^{-1}$), whereas about 70% of the probe is in a highly oxygen sensitive environment ($K_{SV2}$>10% $O_2^{-1}$). In contrast, the xerogel prepared from the same precursor mixture as the aerogel exhibits markedly different quenching behavior, with the vast majority of the signal responsive to changes in oxygen concentration, but with a lower $K_{SV}$ than for the other materials. The presence of even small amounts of oxygen reduces the fluorescence intensity of each of the materials considerably, so these monoliths are well suited to application as switches. Preliminary fluorescence lifetime measurements indicate that there are three different fluorescence lifetimes for $Ru(dpp)_3^{2+}$ in the gels, indicating three microenvironments.

The PtOEP-doped aerogels are suitable for quantitative sensor applications. The response time is comparable to thin-film sol-gel work by others (Del Monte et al., *Langmuir* 16:7377 (2000), which is hereby incorporated by reference in its entirety). A factor of 3.7 increase in signal is observed when the sensor cycles from air to 100% nitrogen. This sensor is less sensitive than some reported in the literature. When Amao et al. immobilized PtOEP in a thin film of poly(styrene-co-pentafluorostyrene) (Amao et al., *Analyst* 125:1911 (2000), which is hereby incorporated by reference in its entirety by reference), they obtained an $F_0/F$ ratio of 18.0 for the fluorescence of PtOEP in 100% argon (0% oxygen) to 100% oxygen. From the fit of the two-site model to the obtained quenching data for the PtOEP-doped aerogel (Table 1), it is apparent that a significant fraction (ca. 20%) of the PtOEP is entrapped in a microenvironment in which it is inaccessible to oxygen quenching.

From the foregoing, it should be appreciated that the $Ru(dpp)_3^{2+}$-doped aerogels and xerogels show promise for use as switches, and the PtOEP-doped aerogels have potential application as quantitative sensors.

While these aerogels are very promising materials for sensor applications, they have been shown to collapse in water. This behavior limits the potential applications of these aerogel-platform $O_2$ (g) sensors, particularly in the field of biosensors, as most biological systems are aqueous. The RSCE process of the present invention has not been fully optimized, and it is possible that optimization of processing parameters will allow more control over the resulting aerogel properties, including the ability to prepare more rugged materials. It will be important to assess the long-term effects of humidity and temperature on sensor stability.

To date, no attempt was made to control the humidity or temperature of the aerogels; they were stored in capped polystyrene cuvettes at room temperature, in a building with only moderate climate control. The same $Ru(dpp)_3^{2+}$-doped aerogels were used over the course of ten months, through four seasons, and no obvious degradation of signal intensity or optical clarity was observed over that time. The doped aerogels are clearly stable; although more controlled studies of temperature and humidity effects are warranted.

Based on the above-described results, it is expected that other probes can be doped into the aerogels to form sensors specialized for other gas-phase molecules, such as carbon monoxide, carbon dioxide, and hydrocarbons.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for rapidly producing aerogels comprising:
   heating and applying external restraining force to a sealed, gas impermeable vessel that contains therein a gel precursor solution or a pre-formed gel that at least partially fills the internal volume of the sealed vessel, said heating and applying external restraining force being carried out without substantial venting of the vessel and thereby confining physical expansion of the gel or gel precursor; and
   controllably releasing the external restraining force applied to the vessel, thereby allowing for venting and release of internal pressure to form the aerogel.

2. The method according to claim 1 wherein said heating and applying restraining force is carried out simultaneously.

3. The method according to claim 1 wherein the applied external restraining force is at least about 70 kN.

4. The method according to claim 1 wherein said heating comprises heating the sealed vessel at a rate of about 1° C. to about 2° C. per minute.

5. The method according to claim 1 further comprising:
   maintaining the temperature and restraining force applied to the sealed vessel for a dwell time prior to said controllably releasing.

6. The method according to claim 5 wherein said maintaining comprises a dwell time of about 1 to about 60 minutes.

7. The method according to claim 6 wherein said maintaining comprises a dwell temperature of about 240 to about 300° C.

8. The method according to claim 1 wherein said controllably releasing comprises removing a portion of the restraining force applied to the sealed vessel.

9. The method according to claim 8 wherein said removing is carried out whereby the remaining force applied to the sealed vessel via the hot plates is at least about 4 kN.

10. The method according to claim 1 wherein the gel or gel precursor comprises one or more chemical sensing agents.

11. The method according to claim 10 wherein the chemical sensing agent is a fluorescent dye or a fluorescent coordination complex.

* * * * *